(12) United States Patent
Yamazaki et al.

(10) Patent No.: US 6,483,484 B1
(45) Date of Patent: Nov. 19, 2002

(54) GOGGLE TYPE DISPLAY SYSTEM

(75) Inventors: Shunpei Yamazaki, Tokyo (JP); Jun Koyama, Kanagawa (JP); Keisuke Hayashi, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/465,493

(22) Filed: Dec. 16, 1999

(30) Foreign Application Priority Data

Dec. 18, 1998 (JP) .......................................... 10-361119

(51) Int. Cl.$^7$ ................................................. G09G 5/00
(52) U.S. Cl. ......................................................... 345/8
(58) Field of Search ............................. 345/7, 8, 82, 83, 345/87, 88, 102; 348/383; 434/307 R

(56) References Cited

U.S. PATENT DOCUMENTS

| 4,149,716 A | 4/1979 | Scudder |
| 4,964,638 A | 10/1990 | Ishida |

(List continued on next page.)

FOREIGN PATENT DOCUMENTS

| JP | 59-186580 | 10/1984 |
| JP | 01-244782 | 9/1989 |
| JP | 02-098386 | 4/1990 |
| JP | 02-297392 | 12/1990 |
| JP | 03-029681 | 2/1991 |
| JP | 03-075078 | 3/1991 |
| JP | 03-286789 | 12/1991 |
| JP | 04-071580 | 3/1992 |
| JP | 04-075674 | 3/1992 |
| JP | 4-208136 | 7/1992 |
| JP | 04-325180 | 11/1992 |
| JP | 04-335730 | 11/1992 |
| JP | 05-003951 | 1/1993 |
| JP | 6-134098 | 5/1994 |
| JP | 8-229236 | 9/1996 |
| JP | 2673768 | 7/1997 |
| JP | 2722302 | 11/1997 |
| JP | 2722303 | 11/1997 |
| JP | 10-92576 | 4/1998 |
| WO | WO 86/01317 | 2/1986 |
| WO | WO 90/13148 | 11/1990 |

OTHER PUBLICATIONS

Inventors: Shunpei Yamazaki et al., "Game Machine" Filing Date: Jul. 16, 2001, Specifications and Drawings for Application Ser. No. 09/904,886.
Inventor: Shunpei Yamazaki, "Game Machine and Game Parlor" Filing Date: Aug. 16, 2001, Specifications and Drawings for Application Ser. No. 09/930,262.

(List continued on next page.)

Primary Examiner—Bipin Shalwala
Assistant Examiner—Jeff Piziali
(74) Attorney, Agent, or Firm—Nixon Peabody LLP; Jeffrey L. Costellia

(57) ABSTRACT

To provide a goggle type display device system that can prevent harm to user's health. If anomaly is recognized in mind and body of a user, first video signals provided from an external device stop being displayed on LCD panels and, instead, outside scenery taken by CCD image capture elements is displayed. The user may be alarmed by this about anomaly of his or her body and, further, relaxed by looking at the outside scenery presented.

48 Claims, 25 Drawing Sheets

U.S. PATENT DOCUMENTS

| | | | |
|---|---|---|---|
| 5,004,238 A | | 4/1991 | Okada |
| 5,007,087 A | | 4/1991 | Bernstein et al. |
| 5,016,879 A | | 5/1991 | Parker et al. |
| 5,048,086 A | | 9/1991 | Bianco et al. |
| 5,060,947 A | | 10/1991 | Hall |
| 5,136,686 A | | 8/1992 | Koza |
| 5,151,900 A | | 9/1992 | Snyder et al. |
| 5,201,321 A | | 4/1993 | Fulton |
| 5,247,190 A | | 9/1993 | Friend et al. |
| 5,255,211 A | * | 10/1993 | Redmond .................. 364/578 |
| 5,270,748 A | | 12/1993 | Katz |
| 5,318,295 A | | 6/1994 | Höfer |
| 5,360,971 A | | 11/1994 | Kaufman et al. |
| 5,362,049 A | | 11/1994 | Höfer |
| 5,395,110 A | | 3/1995 | Yamazaki et al. |
| 5,399,502 A | | 3/1995 | Friend et al. |
| 5,421,576 A | | 6/1995 | Yamazaki et al. |
| 5,560,601 A | | 10/1996 | Yamazaki et al. |
| 5,594,569 A | | 1/1997 | Konuma et al. |
| 5,702,323 A | * | 12/1997 | Poulton ......................... 482/8 |
| 5,735,741 A | | 4/1998 | Yamazaki et al. |
| 5,759,044 A | * | 6/1998 | Redmond .................. 434/307 |
| 5,769,415 A | | 6/1998 | Yamazaki et al. |
| 5,800,265 A | | 9/1998 | Yamazaki et al. |
| 6,000,696 A | | 12/1999 | Yamazaki et al. .......... 273/108 |
| 6,055,027 A | * | 4/2000 | Yamazaki et al. ............ 349/15 |
| 6,066,075 A | * | 5/2000 | Poulton ......................... 482/8 |
| 6,279,902 B1 | | 8/2001 | Yamazaki et al. .......... 273/108 |
| 6,290,601 B1 | | 9/2001 | Yamazaki et al. ............ 463/22 |
| 6,307,948 B1 | * | 10/2001 | Kawasaki et al. .......... 382/100 |

OTHER PUBLICATIONS

Furue et al., "Characteristics and Driving Scheme of Polymer–Stabilized Monostable FLCD Exhibiting Fast Response Time and High Contrast Ratio with Gray–Scale Capability", SID 98 Digest, pp. 782–785.

Yoshida et al., "A Full–Color Thresholdless Antiferroelectric LCD Exhibiting Wide Viewing Angle with Fast Response Time", SID 97 Digest, pp. 841–844.

Inui et al., "Thresholdless Antiferroelectricity in Liquid Crystals and its Application to Displays", J. Mater. Chem., 1996, 6(4), pp. 671–673.

Terada et al., "Half–V Switching Mode FLCD", Proceedings of the 46th Applied Physics Association Lectures, 28P–V–8, p. 1316, Mar. 1999.

Yoshihara et al., "Time Division Full Color LCD by Ferroelectric Liquid Crystal", Ekisho, vol. 3, No. 3, pp. 190–194, 1999.

Hermann Schenk et al., "Polymers for Light Emitting Diodes", EuroDisplay '99 Proceedings, pp. 33–37.

* cited by examiner

GOGGLE TYPE DISPLAY SYSTEM

BACKGROUND OF THE INVENTION

1. Field of the Invention

The present invention relates to a goggle type display device system worn by a user on the head.

2. Description of the Related Art

In recent years, goggle type display devices worn by a user on the head are gaining popularity. Those goggle type display devices, also called as HMDs (head mount displays), have lenses for magnifying an image to form its virtual image and a display devices, such as liquid crystal panels, arranged in a shorter distance than the focal distance of the lenses. A user observes a display on the liquid crystal panels through the lenses to have the magnified image. Thus, in spite of smallness of the devices, the user can enjoy a large screen display.

However, the user, observing the virtual image through the lenses, will have very sore eyes. If this eyestrain lasts while untreated, in the worst cases, user's eyesight may be damaged even by a short time use, which is a problem with those display devices.

SUMMARY OF THE INVENTION

The present invention has been made in view of the above problem and, therefore, an object of the present invention is to provide a goggle type display device system the use of which causes no harm to user's health.

According to the present invention, there is provided a goggle type display device system comprising:
two liquid crystal display devices;
first video signals inputted from an external video signal supplying device;
two image capture elements for converting outside images into second video signals;
a sensor for converting vital information of a user into a vital information signal; and
a video signal control circuit for providing the two liquid crystal display devices with video signals, characterized in that the video signal control circuit provides the two liquid crystal display devices with the first video signals or the second video signals on the basis of an index obtained by numerically processing the vital information signal.

According to the present invention, there is provided a goggle type display device system comprising:
two liquid crystal display devices;
first video signals inputted from an external video signal supplying device;
two first image capture elements for converting outside images into second video signals;
two second image capture elements for converting images of user's eyes into third video signals;
a sensor for converting vital information of a user into a vital information signal; and
a video signal control circuit for providing the two liquid crystal display devices with video signals, characterized in that
the video signal control circuit provides the two liquid crystal display devices with the first video signals or the second video signals on the basis of an index obtained by numerically processing the third video signals and the vital information signal.

According to the present invention, there is provided a goggle type display device system comprising:
two liquid crystal display devices;
first video signals inputted from an external video signal supplying device;
two image capture elements for converting outside images into second video signals;
a sensor for converting vital information of a user into a vital information signal; and
a video signal control circuit for providing the two liquid crystal display devices with video signals, characterized in that:
the video signal control circuit calculates the degree of fatigue of the user on the basis of a chaos attractor index obtained by numerically processing the vital information signal;
the video signal control circuit provides the two liquid crystal display devices with the first video signals when the degree of fatigue is equal to or less than a predetermined level; and
the video signal control circuit provides the two liquid crystal display devices with the second video signals when the degree of fatigue exceeds the predetermined level.

According to the present invention, there is provided a goggle type display device system comprising:
two liquid crystal display devices;
first video signals inputted from an external video signal supplying device;
two image capture elements for converting outside images into second video signals;
another pair of image capture elements for converting images of user's eyes into third video signals;
a sensor for converting vital information of a user into a vital information signal; and
a video signal control circuit for providing the two liquid crystal display devices with video signals, characterized in that:
the video signal control circuit calculates the degree of fatigue of the user on the basis of a chaos attractor index obtained by numerically processing the third video signals and the vital information signal;
the video signal control circuit provides the two liquid crystal display devices with the first video signals when the degree of fatigue is equal to or less than a predetermined level; and
the video signal control circuit provides the two liquid crystal display devices with the second video signals when the degree of fatigue exceeds the predetermined level.

The first image capture elements may be CCD image capture elements or image sensors.

The second image capture elements may be CCD image capture elements or image sensors.

The vital information of a user may be pulse wave, blood pressure, body temperature or dilated degree of the pupils of the eyes.

The sensor may be a pulse wave sensor, a blood pressure sensor or a body temperature sensor.

The pulse wave sensor, the blood pressure sensor or the body temperature sensor may be arranged in headphones.

The image sensors may be formed integrally with the liquid crystal display devices.

The liquid crystal display devices may be reflection type liquid crystal display devices.

The liquid crystal display devices each have a back light that may use red LEDs, green LEDs and blue LEDs.

The liquid crystal display devices may be driven by a field sequential system.

DETAILED DESCRIPTION OF THE PREFERRED EMBODIMENTS

Hereinafter, embodiments of the present invention will be described. Incidentally, following embodiments are examples preferred and are not intended to restrict thereto a goggle type display device system of the present invention.

Embodiment 1

Figure 1:
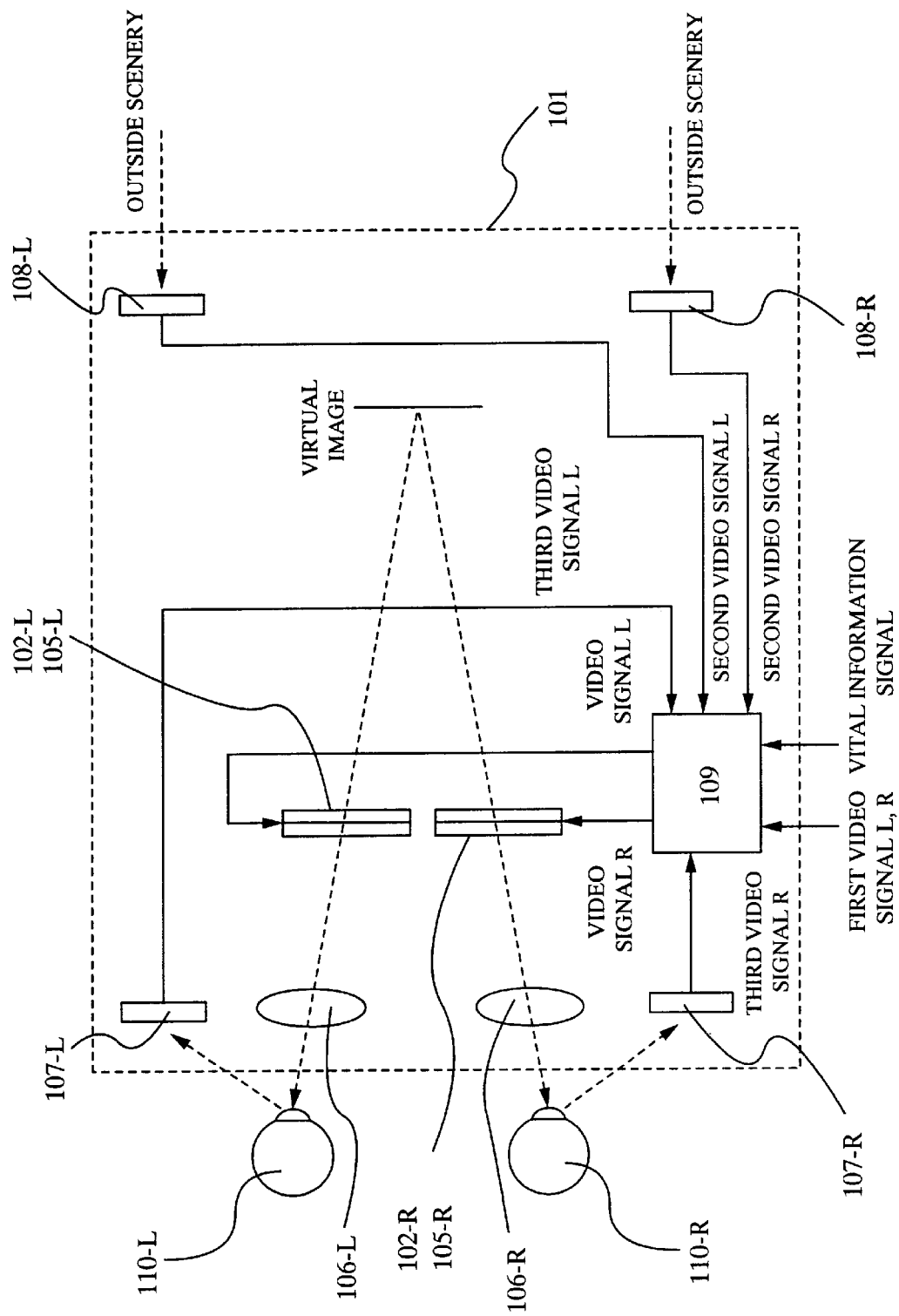
FIG. 1 is a constructional diagram schematically showing a goggle type display device system according to Embodiment 1 of the present invention.

FIG. 1 schematically shows a constructional diagram of a goggle type display device system according to this embodiment. Reference symbol 101 denotes a goggle type display device, and denoted by 102-L and 102-R are LCD panels (liquid crystal panels). Throughout the specification, there can be found reference symbols with appendant characters of "-R" or "-L", which indicates that members denoted by those reference symbols are components either for the right eye or for the left eye. Reference symbols 105-L and 105-R denote LED back lights each having a photoconductive plate 103 (not shown) and an LED 104 (not shown). The LED 104 includes a plurality of LEDs which emit red light, green light and blue light, respectively, and serves as a white light source as a whole. The photoconductive plate 103 is to uniformly irradiate all over the display surfaces of the LCD panels 102 with light emitted from those plural LEDs. Reference symbols 106-L and 106-R denote lenses. Denoted by 107-L and 107-R are CCD image capture elements that capture images of user's left eye and right eye and convert the images into a third video signal L and a third video signal R, respectively. Another pair of CCD image capture elements 108-L and 108-R capture outside scenery (images) and convert it into a second video signal L and a second video signal R, respectively. Inputted to a video signal control circuit 109 are: a first video signal L and a first video signal R which are sent from an external device; a vital information signal of a user; the third video signal L and the third video signal R which are sent from the CCD image capture elements 107-L and 107-R; and the second video signal L and the second video signal R which are sent from the CCD image capture elements 108-L and 108-R. The video signal control circuit 109 provides the LCD panels 102-L and 102-R with a video signal L and a video signal R, respectively. Reference symbols 110-L and 110-R denote user's left eye and right eye, respectively.

The goggle type display system of this embodiment includes, other than those components, a sensor for obtaining vital information of a user and converting it into the vital information signal, speakers or headphones for outputting voice, music and the like, a VCR or a computer for supplying video signals, etc.

Figure 2:
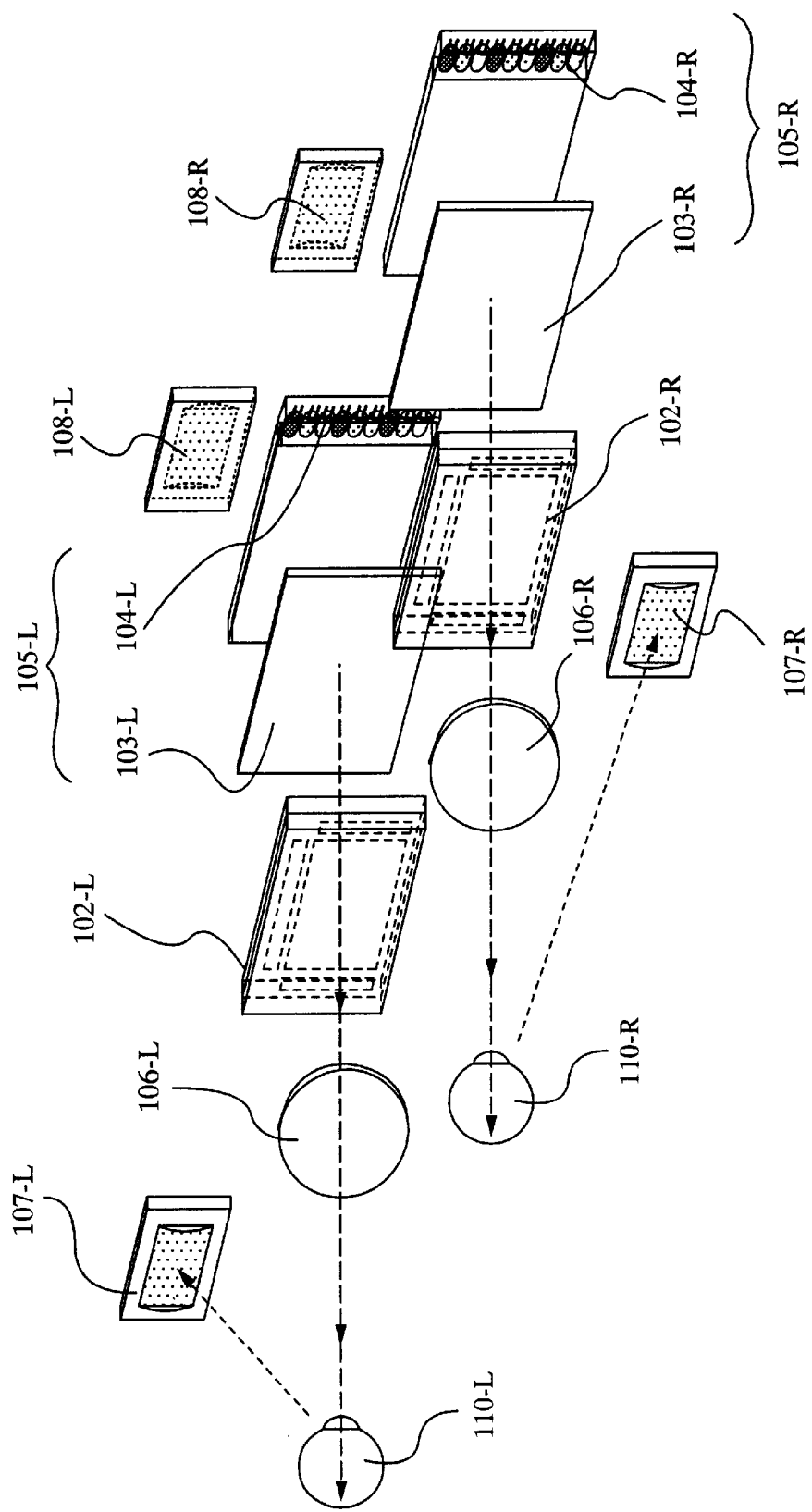
FIG. 2 is a perspective view showing the schematic construction of the goggle type display device system according to Embodiment 1 of the present invention.

FIG. 2 shows in a perspective view the construction of the goggle type display device system of this embodiment shown in FIG. 1.

Figure 3:
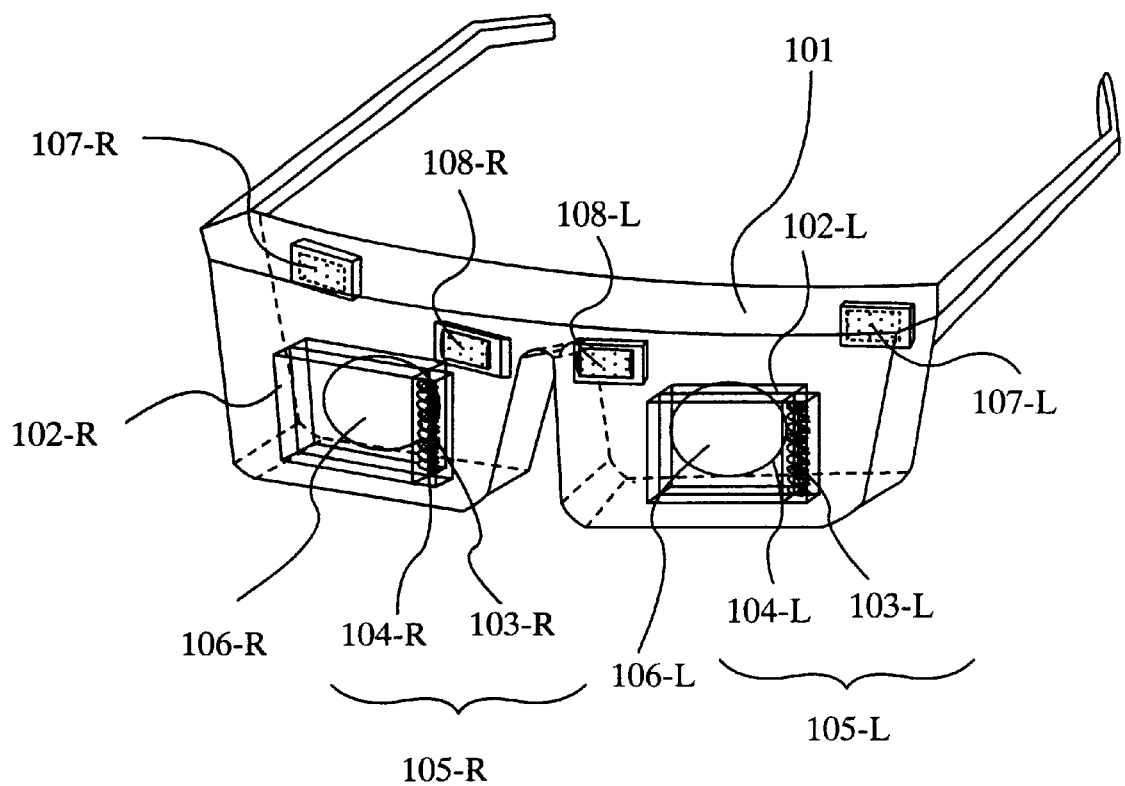
FIG. 3 is a perspective view showing the appearance of the goggle type display device system according to Embodiment 1 of the present invention.

FIG. 3 is a view showing the appearance of the goggle type display device in this embodiment. Drawn as a perspective view, FIG. 3 shows every component of the device.

The arrangement in FIG. 3 does not limit the arrangement of the CCD image capture elements 107-L, 107-R for monitoring user's eyes and of the CCD image capture elements 108-L, 108-R for capturing outside images. Depending on design, the arrangement of these CCD image capture elements may be changed.

In this embodiment, display is accomplished by driving the LCD panels with the field sequential method, using the LED back lights.

Figure 18:
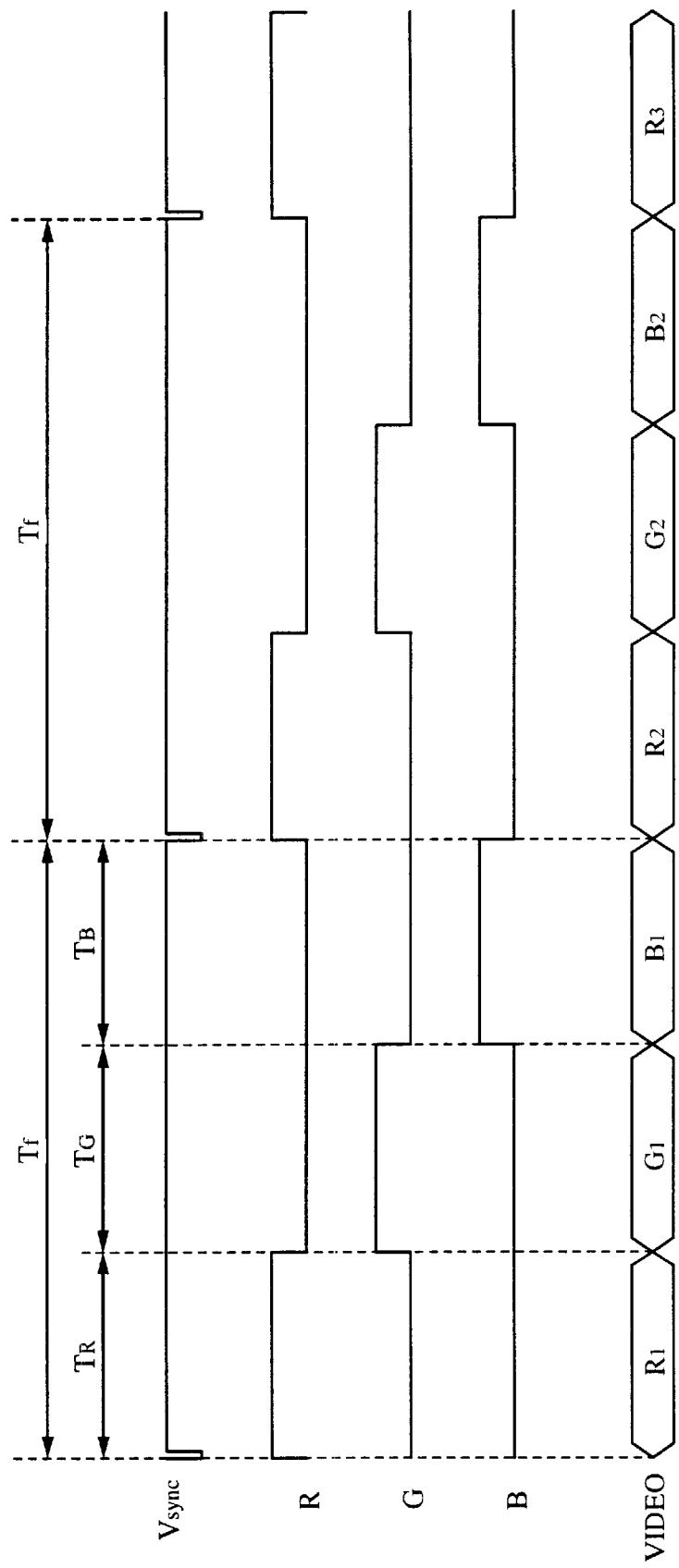
FIG. 18 is a timing chart of a field sequential driving method of Embodiment 1 of the present invention.

FIG. 18 shows a timing chart of the field sequential driving method. In the timing chart of the field sequential driving method, there are shown a starting signal for video signal writing (V sync signal), lighting timing signals for red (R), green (G) and blue (B) LEDs, and a video signal (VIDEO). Tfs indicate frame periods. TR, TG and TB indicate LED lit-up periods of red (R), green (G) and blue (B), respectively.

Of the video signals supplied to the LCD panels, for example, R1 is a signal that is compressed in time-base to have a ⅓ size of an original video signal inputted from the external and corresponding to red; G1 is a signal that is compressed in time-base to have a ⅓ size of an original video signal inputted from the external and corresponding to green; and B1 is a signal that is compressed in time-base to have a ⅓ size of an original video signal inputted from the external and corresponding to blue.

In the field sequential driving method, the LEDs of R, G and B are lit up in order during the LED lit-up periods, i.e., TR period, TG period and TB period, respectively. During the lit-up period of the red LED (TR), a video signal corresponding to red (R1) is supplied to the LCD panels to write therein a red image for one screen. During the lit-up period of the green LED (TG), a video signal corresponding to green (G1) is supplied to the LCD panels to write therein a green image for one screen. During the lit-up period of the blue LED (TB), a video signal corresponding to blue (B1) is supplied to the LCD panels to write therein a blue image for one screen. Formation of one frame takes these three times operations of image writing.

Therefore, a color LCD panel driven by the field sequential driving method can acquire a resolution three times as high as that of a conventional color display device.

Incidentally, a back light of a cathode-ray tube may be used to display in the goggle type display device of the present invention.

Here, operation and function of the goggle type display system of this embodiment will be described. See once more FIG. 1. According to the goggle type display system of this embodiment, in a normal use, the video signal control circuit provides the LCD panels 102-L and 102-R with, respectively, the first video signal L and the first video signal R which are supplied from an external device. As an example of the external device, a personal computer, a portable information terminal and a VCR are enumerated. A user observes an image displayed on the LCD panels 102-L and 102-R through the lenses 106-L and 106-R. The user sees the image displayed on the LCD panels as a magnified image (virtual image) in a location far away from the actual position of the LCD panels.

The goggle type display device 101 of this embodiment is equipped with the CCD image capture elements 107-L and 107-R for monitoring eye balls of a user and for converting the images of the eyes into electric signals. These CCD image capture elements 107-L and 107-R monitor the images of user's eyes during the device is in use, and input video signals of the eyes (third video signals) to the video signal control circuit 109. The video signal control circuit 109 numerically processes the input video signals of the eyes (third video signals) to calculate the degree of congestion in the user's eyes.

Figure 4:
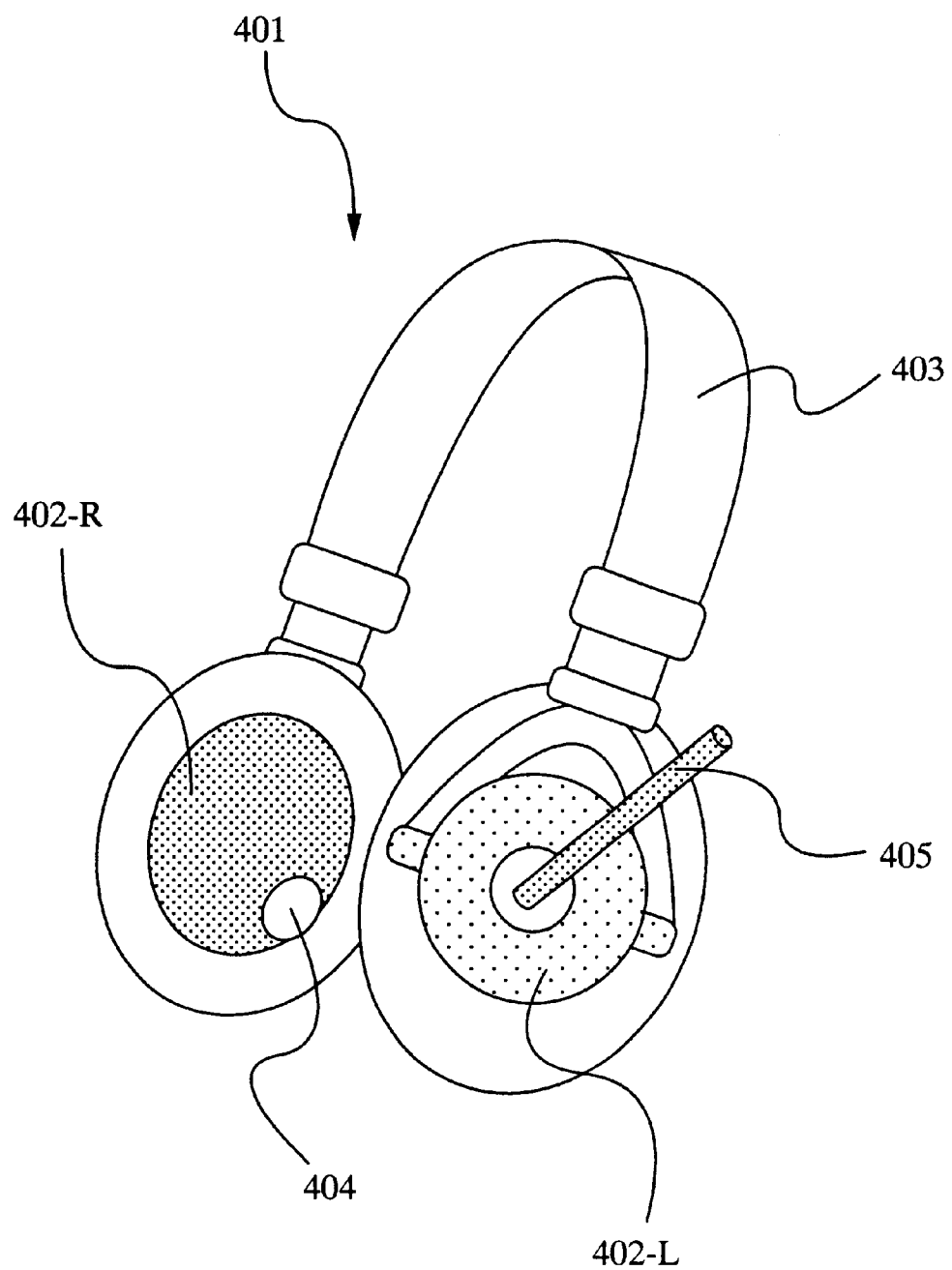
FIG. 4 is a view showing headphones for use in a goggle type display device system of Embodiment 1 of the present invention.

The goggle type display device system of this embodiment comprises headphones 401 as shown in FIG. 4. In FIG. 4, reference symbols 402-R and 402-L denote speaker units. A band is designated by 403. Denoted by 404 is a pulse wave sensor made to fit to a part of user's ear for detecting the pulse wave of the user. Antenna 405 receives voices and music on electric waves from the external device and transmits information on the user's pulse waves detected by the pulse wave sensor to the video signal control circuit 109 of the goggle type display device 101.

Figure 5:
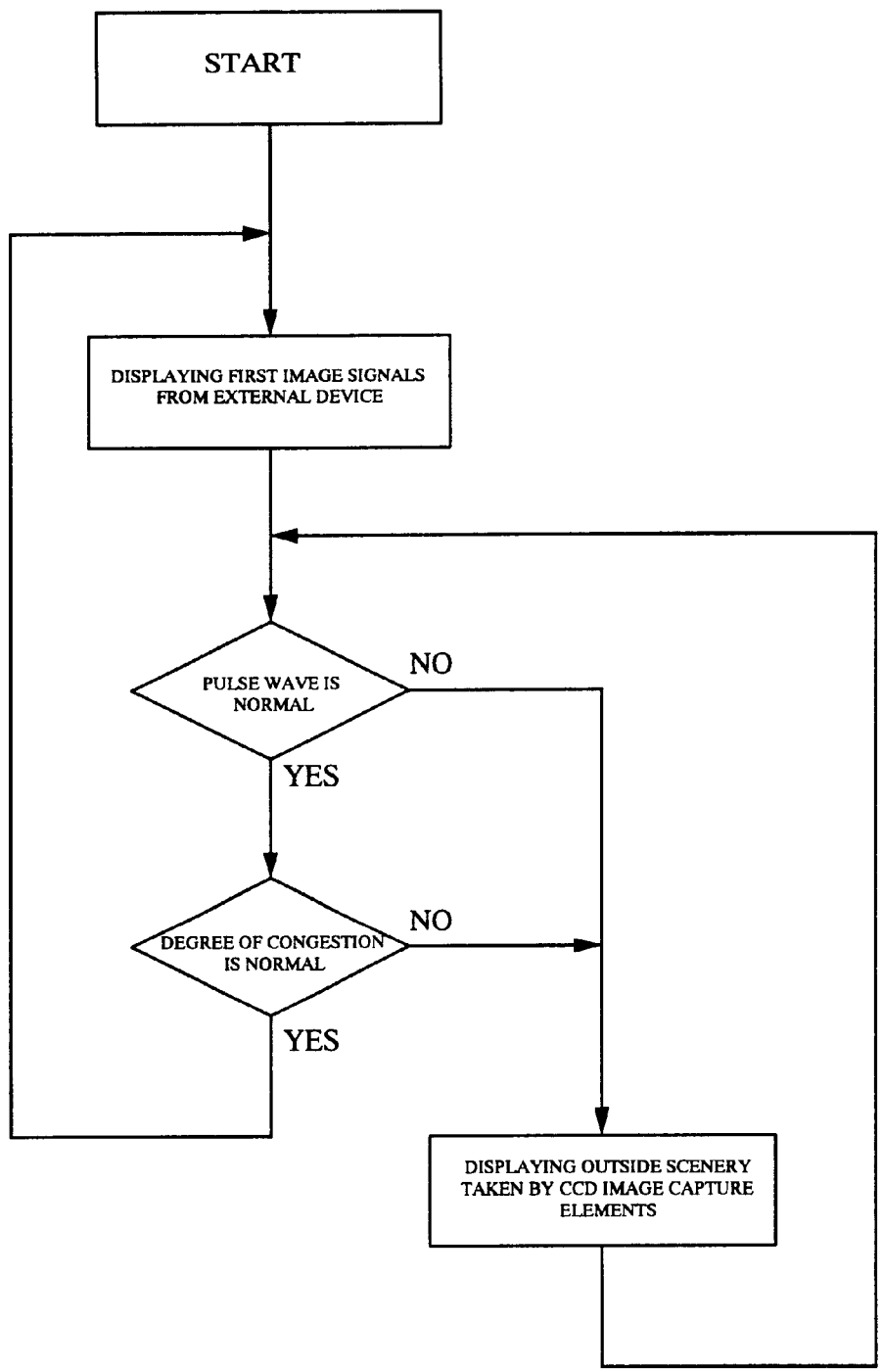
FIG. 5 is a flow chart showing the operation of the goggle type display device system according to Embodiment 1 of the present invention.

Referring to FIG. 5, there is shown a operational flow chart of the goggle type display device system according to this embodiment. In the goggle type display device system according to this embodiment, normally, the video signal control circuit provides the LCD panels with the first image signals sent from the external device (such as a personal computer or a VCR). The pulse wave information measured by the pulse wave sensor that is attached to the headphones is inputted to the video signal control circuit 109. Though vital information signals from the sensor is inputted to the video signal control circuit 109 in this embodiment, the vital information signals from the sensor may be sent once to the external device to be then inputted from the external device to the video signal control circuit 109.

When the pulse wave of the user is smaller than a predetermined value, the system judges that "the pulse wave is normal" and proceeds to the next step. When the pulse wave of the user is larger than the predetermined value, the system judges that "the pulse wave is abnormal" and outside scenery taken by the CCD image capture elements 108-L and 108-R is displayed on the LCD panels.

The images of the user's eyes captured by the CCD image capture elements 107-L and 107-R are, after converted into video signals, inputted to the video signal control circuit 109. The video signal control circuit 109 performs image processing on the video signals of the user's eyes to calculate the degree of congestion in the user's eyes.

When the degree of congestion in the user's eyes which is calculated on the basis of the video signals of the user's eyes is smaller than a predetermined value, the system judges that "the degree of congestion is normal" and proceeds to the next normal step. When the degree of congestion in the user's eyes is larger than the predetermined value, the system judges that "the degree of congestion is abnormal" and outside scenery taken by the CCD image capture elements 108-L and 108-R is displayed on the LCD panels.

The above operations are repeated.

Figure 14:
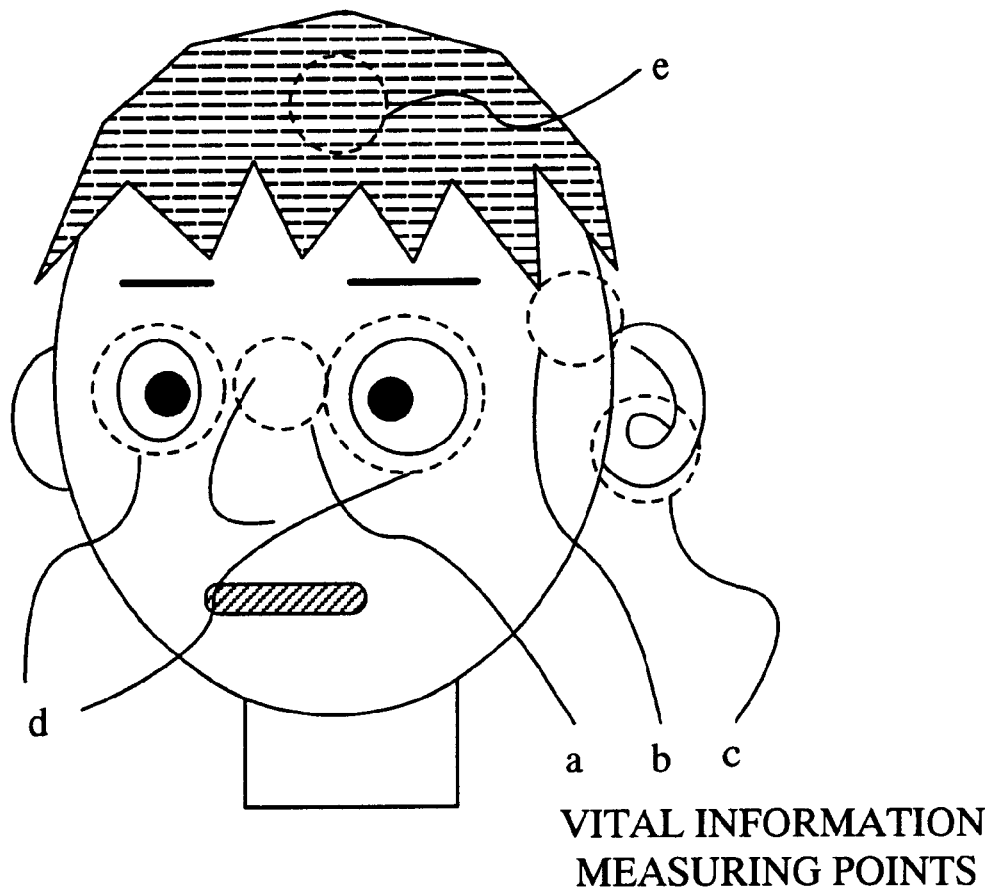
FIG. 14 is a view showing exemplary points of measurement for obtaining vital information of a user, which is utilized in a goggle type display device system of Embodiment 1 of the present invention.

As shown in FIG. 14, vital information of a user can be obtained from various regions of user's body (regions a to e, and others).

If pulse wave anomaly or eye congestion anomaly of the user is recognized, as described above, the first video signals provided from the external device stop being displayed on the LCD panels and outside scenery taken by the CCD image capture elements 108-L and 108-R is displayed instead. The user may be alarmed by this about anomaly of his or her body and, further, relaxed by looking at the outside scenery presented.

Embodiment 2

In this embodiment, a description will be given on a case where a blood pressure sensor is installed in addition to the structure of the goggle type display device of the above Embodiment 1. Incidentally, Embodiment 2 is the same as Embodiment 1 except for the installment of the blood pressure sensor, and hence Embodiment 1 can be referred with regard to the detailed structure of this embodiment.

Figure 6:
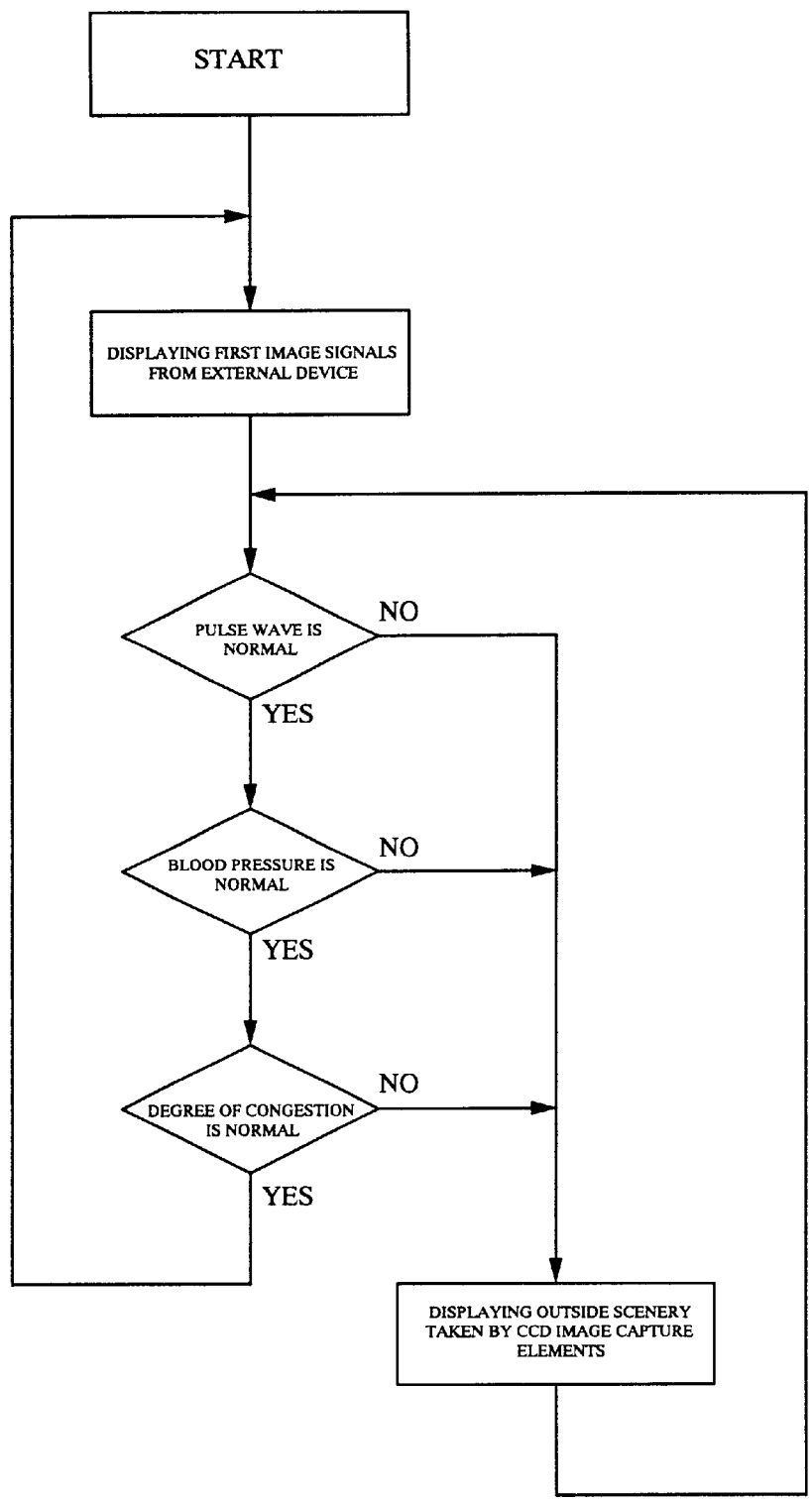
FIG. 6 is a flow chart showing the operation of the goggle type display device system according to Embodiment 2 of the present invention.

Referring to FIG. 6, the drawing shows an operational flow chart of a goggle type display device system of this embodiment. According to the goggle type display system of this embodiment, in a normal use, a video signal control circuit provides LCD panels 102-L and 102-R with first video signals L and R that are supplied from an external device.

As described in Embodiment 1, when the pulse wave of a user is smaller than a predetermined value, the system judges that "the pulse wave is normal" and proceeds to the next normal step. When the pulse wave of a user is larger than the predetermined value, the system judges that "the pulse wave is abnormal" and outside scenery taken by CCD image capture elements 108-L and 108-R is displayed on the LCD panels.

Then, information about user's blood pressure is obtained from a sensor. This blood pressure information is inputted to the video signal control circuit. When the user's blood pressure is smaller than a predetermined value, the system judges that "the blood pressure is normal" and proceeds to the next step. When the user's blood pressure is larger than the predetermined value, the system judges that "the blood pressure is abnormal" and outside scenery taken by the CCD image capture elements 108-L and 108-R is displayed on the LCD panels.

When the degree of congestion in user's eyes which is calculated on the basis of the video signals of the user's eyes is smaller than a predetermined value, the system judges that "the degree of congestion is normal" and proceeds to the next normal step. When the degree of congestion in the user's eyes is larger than the predetermined value, the system judges that "the degree of congestion is abnormal" and outside scenery taken by the CCD image capture elements 108-L and 108-R is displayed on the LCD panels.

Thus, in this embodiment also, upon recognition of pulse wave anomaly, blood pressure anomaly or eye congestion anomaly of the user, displaying on the LCD panels the first video signals supplied from the external device is stopped and outside scenery taken by the CCD image capture elements 108-L and 108-R is displayed instead. The user may be alarmed by this about anomaly of his or her body and, further, relaxed by looking at the outside scenery presented.

Embodiment 3

A goggle type display device system of this embodiment is the same in structure as the goggle type display device system of the above Embodiment 1. However, the system of this embodiment uses chaos theory to decide, on the basis of user's vital information, whether or not switching from an image sent from an external device to outside image sent from CCD image capture elements is needed.

Figure 7:
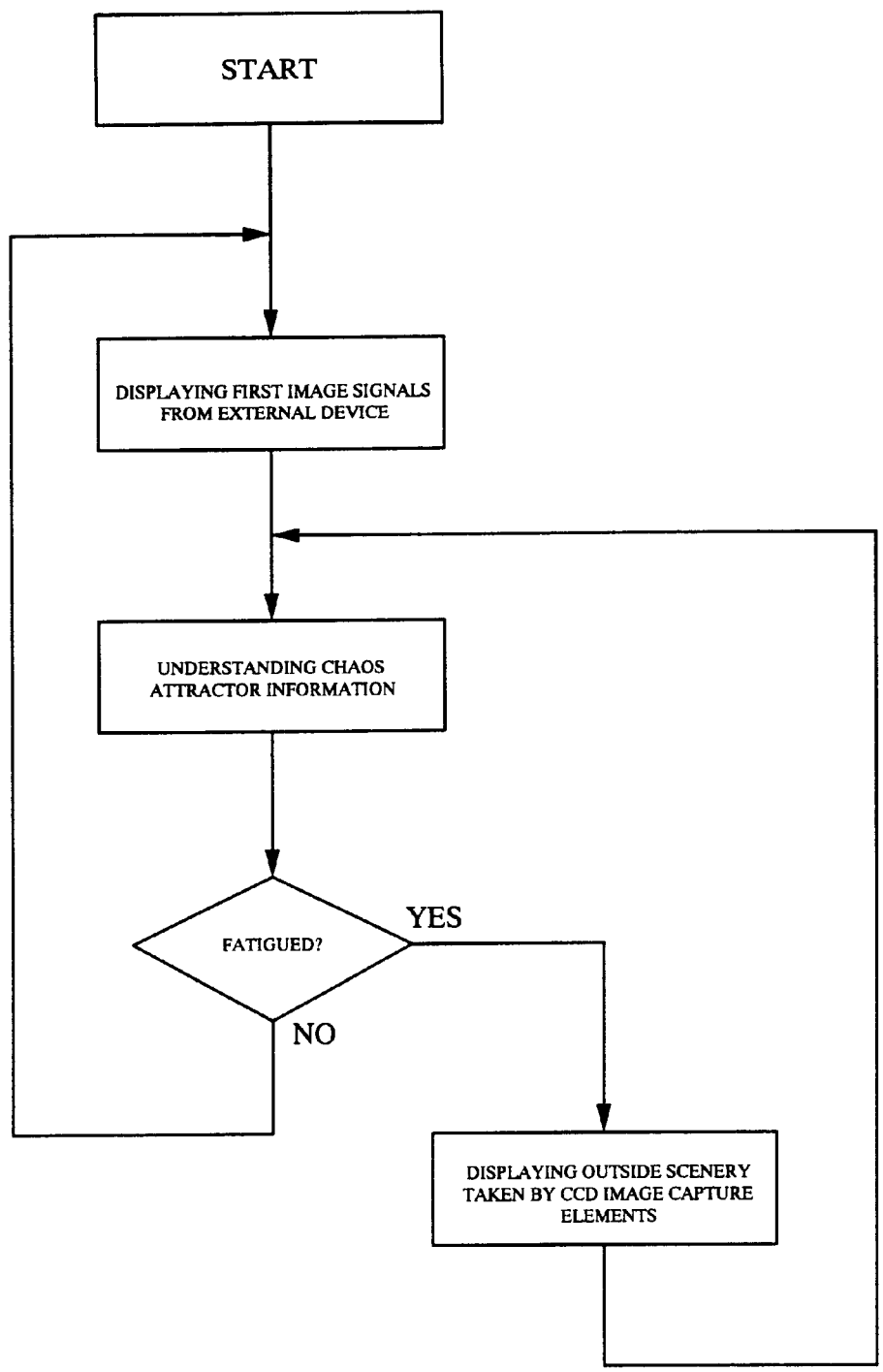
FIG. 7 is still a flow chart showing the operation of the goggle type display device system according to Embodiment 3 of the present invention.

Reference is made to FIG. 7. The goggle type display device system of this embodiment obtains chaos attractor information on the basis of the vital information presented by a pulse wave sensor, a blood pressure sensor, a body temperature sensor or CCD image capture elements that capture images of user's eyes.

First of all, what "chaos" designates is explained. In nature or in an artificial world, there are a lot of predictable phenomena. For instance, Halley's comet or an operating artificial satellite is one of such phenomena, and to predict the comet's or satellite's location and act correspondingly is within the realm of possibility. We might see it is the deterministic predictability, where there is no indefinition between cause and effect, that forms an aspect of the great power of science.

However, weather is often forecasted wrong despite the assumption that it is the motion of the atmosphere which obeys the physical law. It has been said that such a phenomenon as weather in which causal relation seems unclear includes disorderly factors, and the phenomenon has been believed to be correctly predicted if, basically, a perfect parameter for describing the system is known. In other words, if it is possible to collect sufficient information about the system.

Namely, the disorderliness has been considered as a result of lack of information about the multi-degree-of-freedom system. Against that notion, the discovery of the fact that even a simple system having merely small degree of freedom (third dimension or higher) sometimes acts disorderedly leads to finding of the existence of what seems to follow determinism but is disorderly in essence. The disorderliness as such has become called chaos.

The concept of chaos, however, has not been standardized yet. It covers vast definition range as does the theory of evolution and, depending on objects, it even gives us the impression that the concept gets ahead of us. Therefore, this specification dares to settle on the concept of chaos as follows.

The chaos means a phenomenon that is random in essence for its very intricate behavior occurring non-linearly despite being a system with a deterministic law. The chaos further implies that a complex order and law may exist behind a seemingly disorderly or orderless phenomenon that lacks any law and predictability.

The topology that characterizes the behavior of chaos is called chaos attractor, which is a mathematical structure where the system behavior generating chaos converges.

From those points of view, the pulse wave detected in a body is known to act chaotically. A recognized authority in this field reported at an academic meeting that finger tip pulse wave showed chaos mental and physical information. At the same time, a medical diagnostic method utilizing that chaos was filed for patent by this person (Japanese Patent Application Laid-open No. Hei 4-208136).

Then, the goggle type display device system of this embodiment actively utilizes the fact that the chaos attractor obtained by numerically processing user's vital information such as pulse wave or blood pressure and Lyapunov index indicating to what degree this data fits the definition condition of the chaos are correlated to mental and physical information of a user.

Based on this, vital information of the user is obtained by forming chaos attractor from numerically processing user's pulse wave, blood pressure, degree of eye congestion, body temperature, etc. The obtained vital information and Lyapunov index that is a numeric value showing to what degree this data fits the definition condition of the chaos are used to know mental and physical conditions of the user.

An example of means for obtaining the pulse wave includes a sensor that has a combination of an infrared light emitting diode and a photo sensor, and one that utilizes a semiconductor pressure sensor.

Here, the relationship between the mental and physical conditions and the chaos attractor of the pulse wave is as follows.

(1) The chaos attractor of the pulse wave acutely reflects the mental state and shows the peculiar topology.

(2) The chaos attractor obtained from the pulse wave has, in addition to the basic structure common to human, a personal structure of his/her own, and varies depending on the mental state or on illness.

(3) Generally, when the mental state or physiological state is unstable or during illness, the whole structure of the attractor becomes simple, small and structureless. Further, the rhythm takes mechanical and monotonous periodic structure. Namely, the attractor becomes less chaotic.

(4) In good health, the whole structure is complicated and dynamic, and the local structure is also complicated to exhibit a wound, twisted or screwed structure. And the rhythm becomes aperiodic. Namely, life in good health is fully chaotic.

(5) When one concentrates his or her mind on something, the chaos attractor becomes complicated and local structure such as wound or twisted structure appears. On the other hand, when one is put under a stress exceeding a certain threshold to feel tired, the structure gets simple and the local structure is lost.

Based on what is expressed in the above items, current condition of a user is classified into several types. An image displayed on the LCD panels is switched in accordance with the classification.

Here, reference is again made to FIG. 7. The goggle type display device of this embodiment normally provides the LCD panels with video signals from the external device.

Vital information (pulse wave, blood pressure, body temperature, etc.) obtained from a user is inputted in a video signal control circuit. The video signal control circuit numerically processes the vital information, judges to which level that is previously set the resulting value corresponds, and calculates Lyapunov index on the basis of that corresponding level. This numerical arithmetic processing and calculation of Lyapunov index require computer processing. However, this processing method and the expression for chaos attractor after processing do not involve with any fixed equation, nor processing procedure, and may be expressed arbitrarily.

The level previously set to calculate Lyapunov index may have as many stages as suited, depending on how to classify or sort the chaos attractor. For example, the classifications "stimulated" and "not stimulated" make two stages. To add to the two stages the classifications "mind concentrated" and "mind distracted" makes the total of four stages. The classifications "fatigued" and "not fatigued" may be added thereto to make the total of six stages. At this stage, an image to be supplied to the LCD panels is switched. That is, when a user is in the "fatigued" stage, first video signals supplied from the external device stop being displayed on the LCD panels and outside scenery taken by CCD image capture elements 108-L and 108-R is displayed instead. The user may be alarmed by this about anomaly of his or her body and, further, relaxed by looking at the outside scenery presented.

As to the chaos theory, techniques disclosed in the following documents by the present applicant may be applied: U.S. Pat. Nos. 5,395,110 and 5,800,265, Japanese Patent Nos. 2722302, 2673768 and 2722303, and Japanese Patent Application Laid-open Nos. Hei 6-134098 and Hei 8-229236.

Embodiment 4

Figure 8:
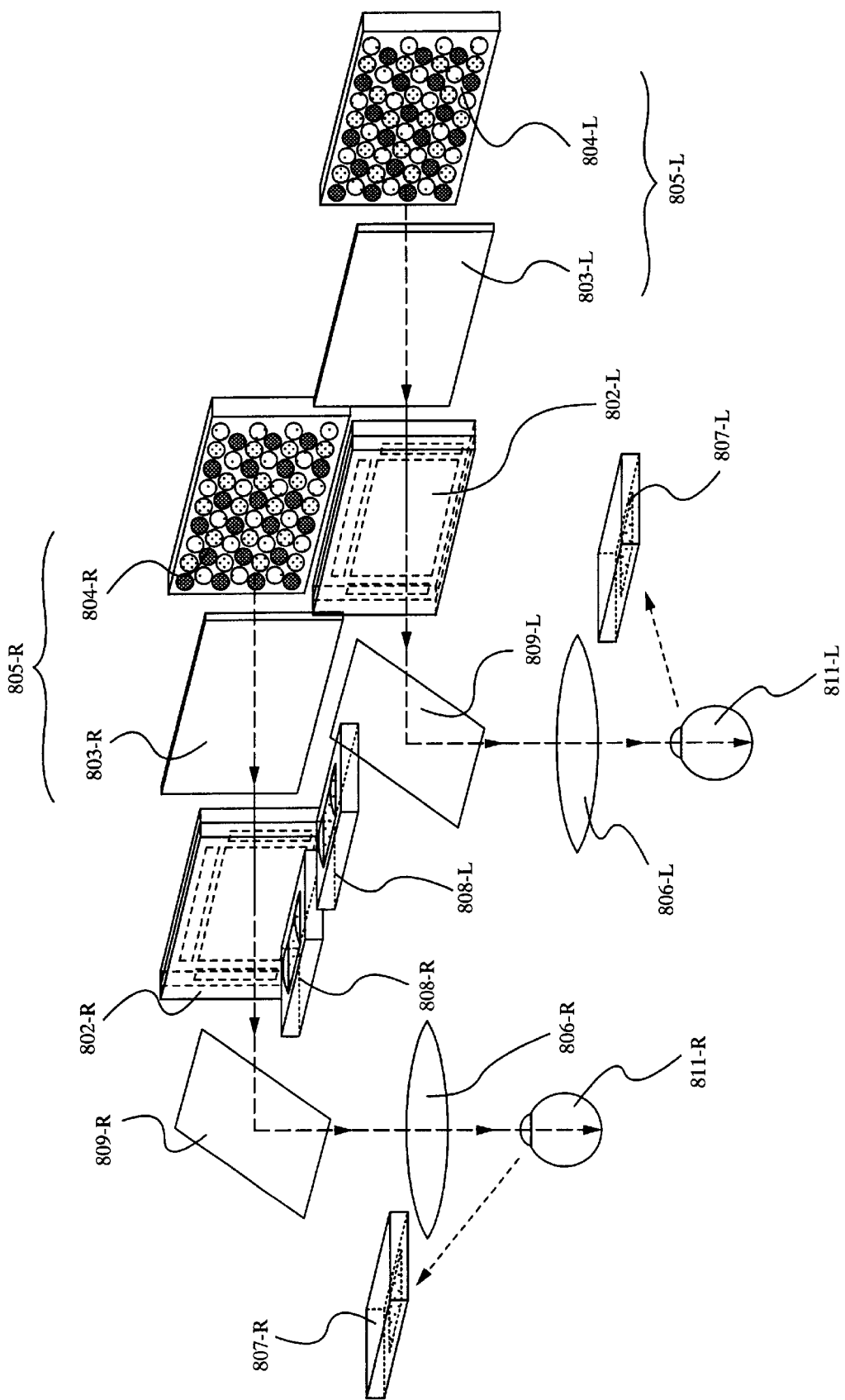
FIG. 8 is a perspective view showing the schematic construction of a goggle type display device system according to Embodiment 4 of the present invention.

A goggle type display system of this embodiment is slightly different in structure from the goggle type display device systems described in the above Embodiments 1 to 3. A perspective view in FIG. 8 shows a schematic constructional diagram of the goggle type display device system of this embodiment. Reference symbols 802-L, 802-R denote LCD panels; 803-L, 803-R, photoconductive plates; and 804-L, 804-R, LEDs. The photoconductive plates 803-L, 803-R and the LEDs 804-L, 804-R constitute LED back lights 805-L, 805-R. The LEDs 804 include a plurality of red LEDs, green LEDs and blue LEDs and, as a whole, serve as white light sources. The photoconductive plates 803 are to uniformly irradiates the LCD panels 802 with light emitted from the plural LEDs. Denoted by 806-L, 806-R are lenses; 807-L, 807-R, CCD image capture elements for capturing images of user's left and right eyes to convert the images into a third video signal L and a third video signal R, respectively; 808-L, 808-R, another pair of CCD image capture elements for taking outside scenery (images) to convert it into a second video signal L and a second video signal R, respectively; and 809-L, 809-R, mirrors for making images on the LCD panels enter into the lenses.

Though not shown in FIG. 8, the goggle type display device of this embodiment has a video signal control circuit 810. The video signal control circuit 810 receives inputs from the external, that is, first video signals from an external device, a vital information signal of a user, the third video signal L and third video signal R from the CCD image capture elements 807-L, 807-R, and the second video signal L and second video signal R from the CCD image capture elements 808-L, 808-R. Also, the video signal control circuit 810 provides the LCD panels 802-L, 802-R with a video signal L and a video signal R.

The goggle type display system of this embodiment comprises, other than these components, a sensor for obtaining user's vital information to convert it into the vital information signal, speakers or headphones for outputting voice or music, etc.

Figure 9:
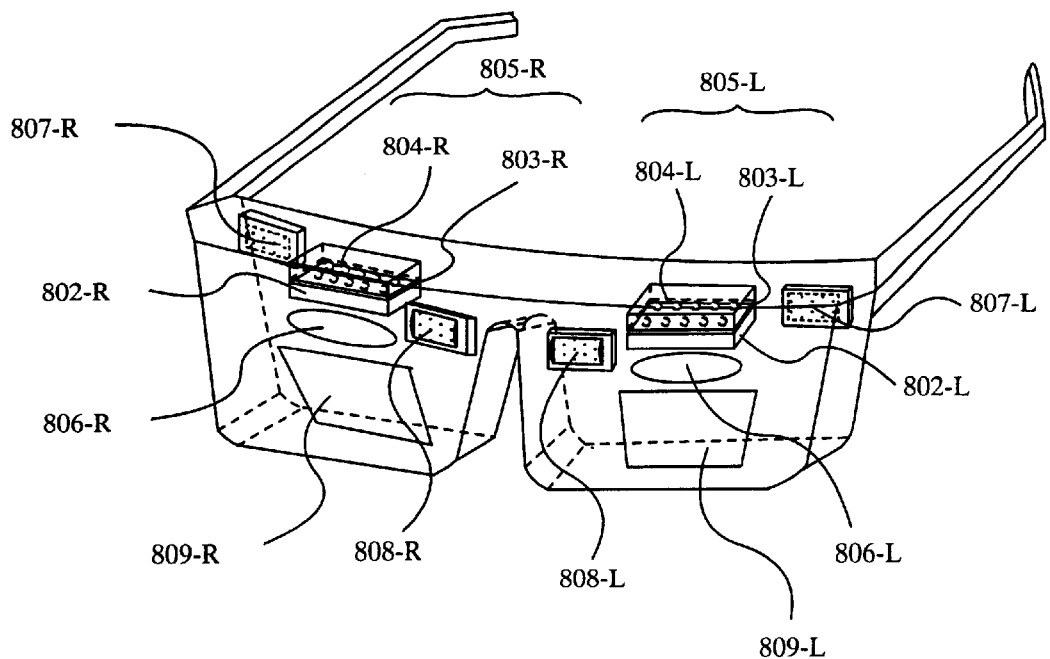
FIG. 9 is a perspective view showing the appearance of the goggle type display device system according to Embodiment 4 of the present invention.

FIG. 9 is a view showing the appearance of the goggle type display device of this embodiment. Drawn as a perspective view, FIG. 9 shows every component of the device.

Incidentally, arrangement of the CCD image capture elements 807-L, 807-R for monitoring user's eyes and CCD image capture elements 808-L, 808-R for taking outside images is not limited to the one shown in FIG. 8. Depending on design, the arrangement of these CCD image capture elements may be changed.

Though LED back lights are used for back lights of the LCD panels in the goggle type display device of this embodiment, cathode-ray tube back lights may be used instead.

Any of the above Embodiments 1 to 3 may be referred with regard to the operation of the goggle type display device of this embodiment.

Embodiment 5

In a goggle type display device of this embodiment, CCD image capture elements for monitoring user's eyes are omitted and, instead, image sensors integrally formed on LCD panels are used to monitor user's eyes.

Figure 10:
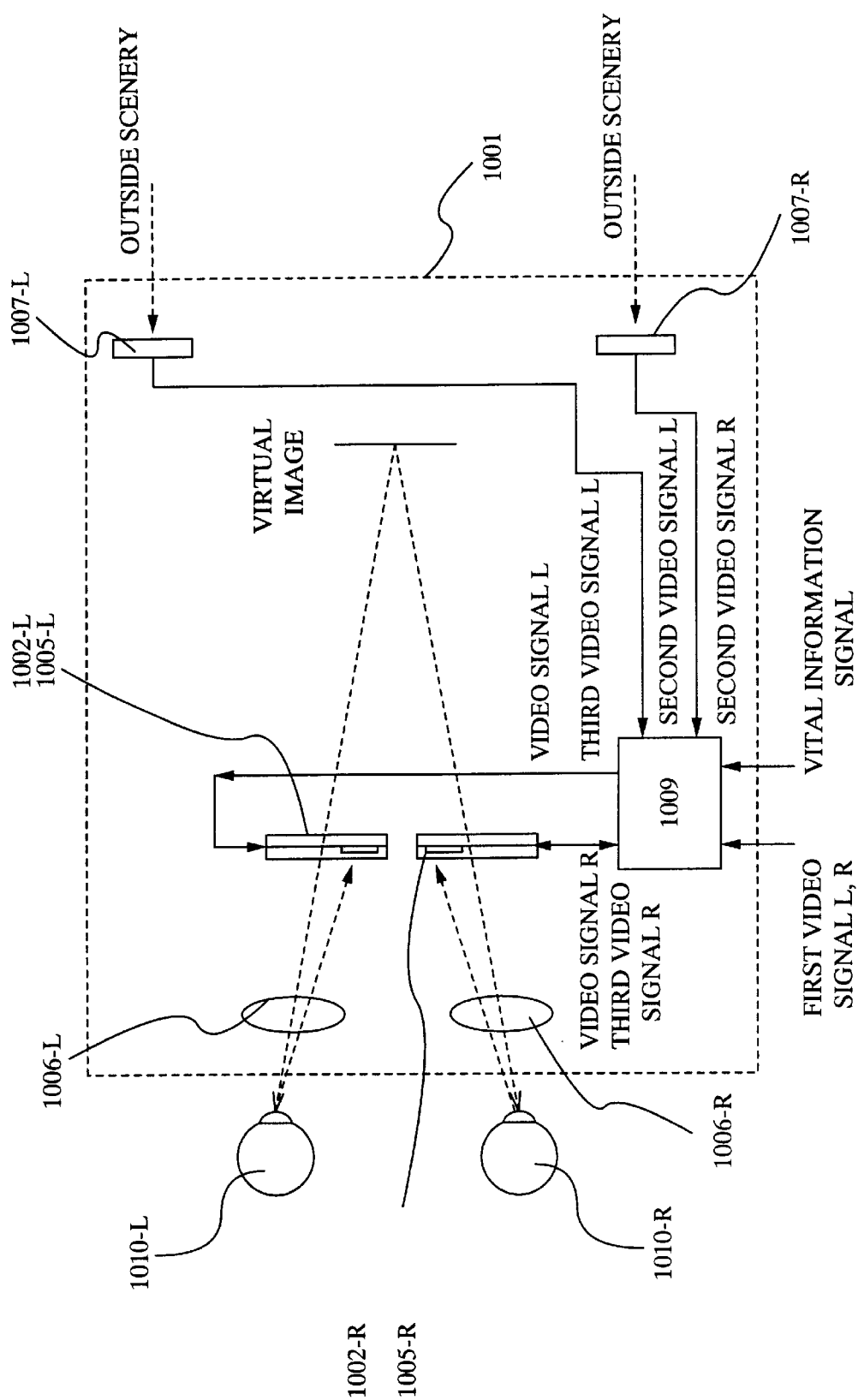
FIG. 10 is a view showing the schematic construction of a goggle type display device system according to Embodiment 5 of the present invention.

FIG. 10 is a schematic constructional diagram showing a goggle type display device system of this embodiment. Reference symbol 1001 denotes a goggle type display device and 1002-L, 1002-R denote LCD panels with built-in image sensors. The image sensors incorporated in the LCD panels 1002-L and 1002-R convert images of user's eyes into a third video signal L and the third video signal R, respectively. Reference symbols 1005-L, 1005-R denote LED back lights each having a photoconductive plate 1003 (not shown) and an LED 1004 (not shown). Lenses are denoted by 1006-L and 1006-L. CCD image capture elements 1007-L, 1007-R take outside scenery (images) to convert it into a second video signal L and a second video signal R. Reference symbol 1009 denotes a video signal control circuit that receives inputs from the external, namely, first video signals from an external device, a vital information signal of a user, the second video signal L and second video signal R from the CCD image capture elements 1007-L, 1007-R, and the third video signal L and third video signal R from the image sensors incorporated in the LCD panels 1002-L, 1002-R. Also, the video signal control circuit 1009 provides the LCD panels 1002-L, 1002-R with a video signal L and a video signal R.

The goggle type display system of this embodiment comprises, other than these components, a sensor for obtaining user's vital information to convert it into a vital information signal, speakers or headphones for outputting voice or music, etc.

Figure 11:
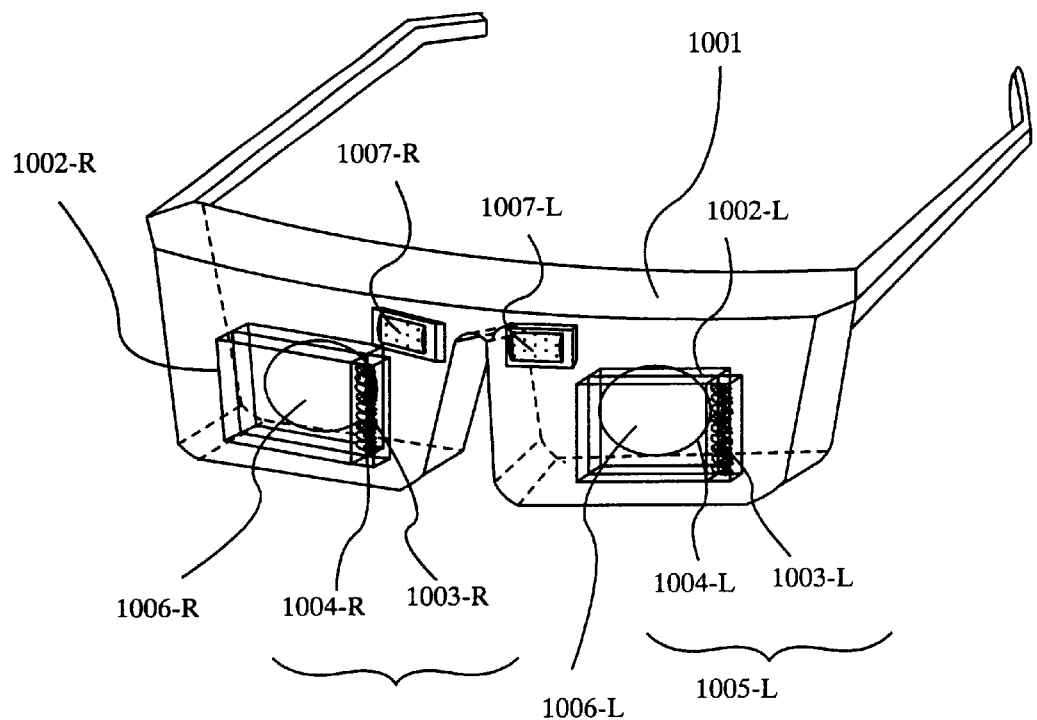
FIG. 11 is a perspective view showing the appearance of the goggle type display device system according to Embodiment 5 of the present invention.

FIG. 11 shows in perspective view the structure of the goggle type display device system of this embodiment shown in FIG. 10.

Figure 15:
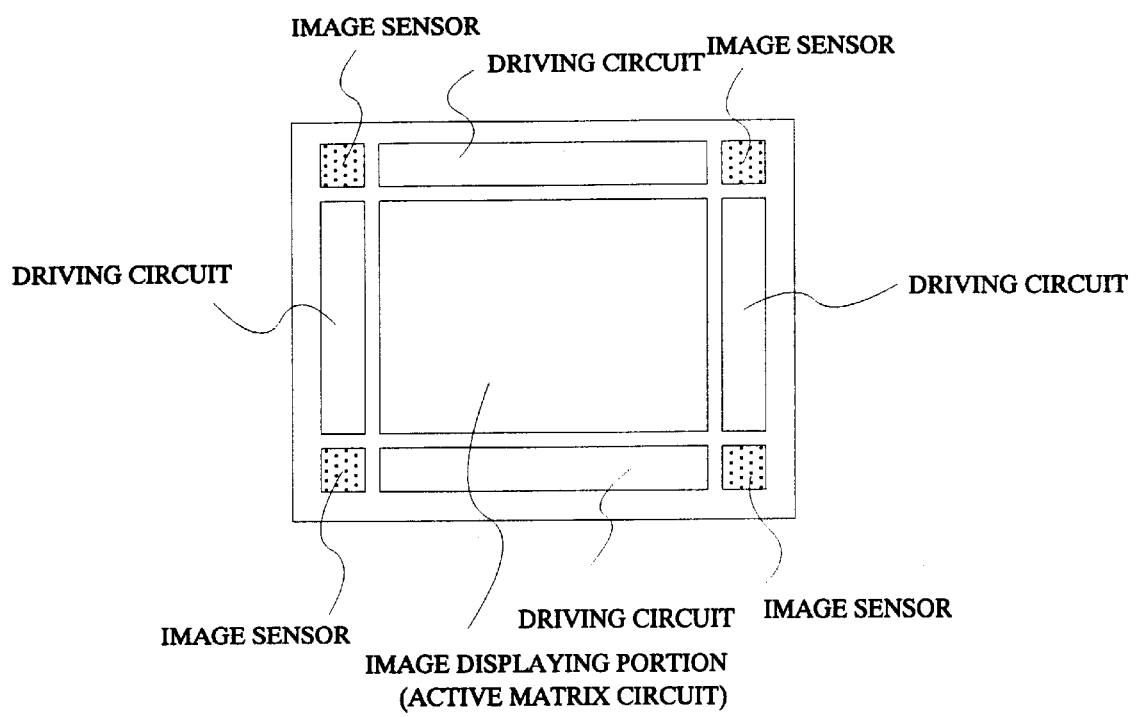
FIG. 15 shows an example of an LCD panel with built-in image sensors for use in the goggle type display device system according to Embodiment 5 of the present invention.

FIG. 15 shows an example of the LCD panels with built-in image sensors used in the goggle type display system of this embodiment. Though the LCD panel shown in FIG. 15 has four relatively small image sensors incorporated therein, the panels are not limited to this example.

Any of the above Embodiments 1 to 3 may be referred with regard to the operation of the goggle type display device of this embodiment.

Embodiment 6

In a goggle type display device of this embodiment, CCD image capture elements for monitoring user's eyes and CCD image capture elements for monitoring outside scenery are omitted and, instead, image sensors integrally formed on the LCD panels are used to monitor user's eyes and outside scenery.

Figure 12:
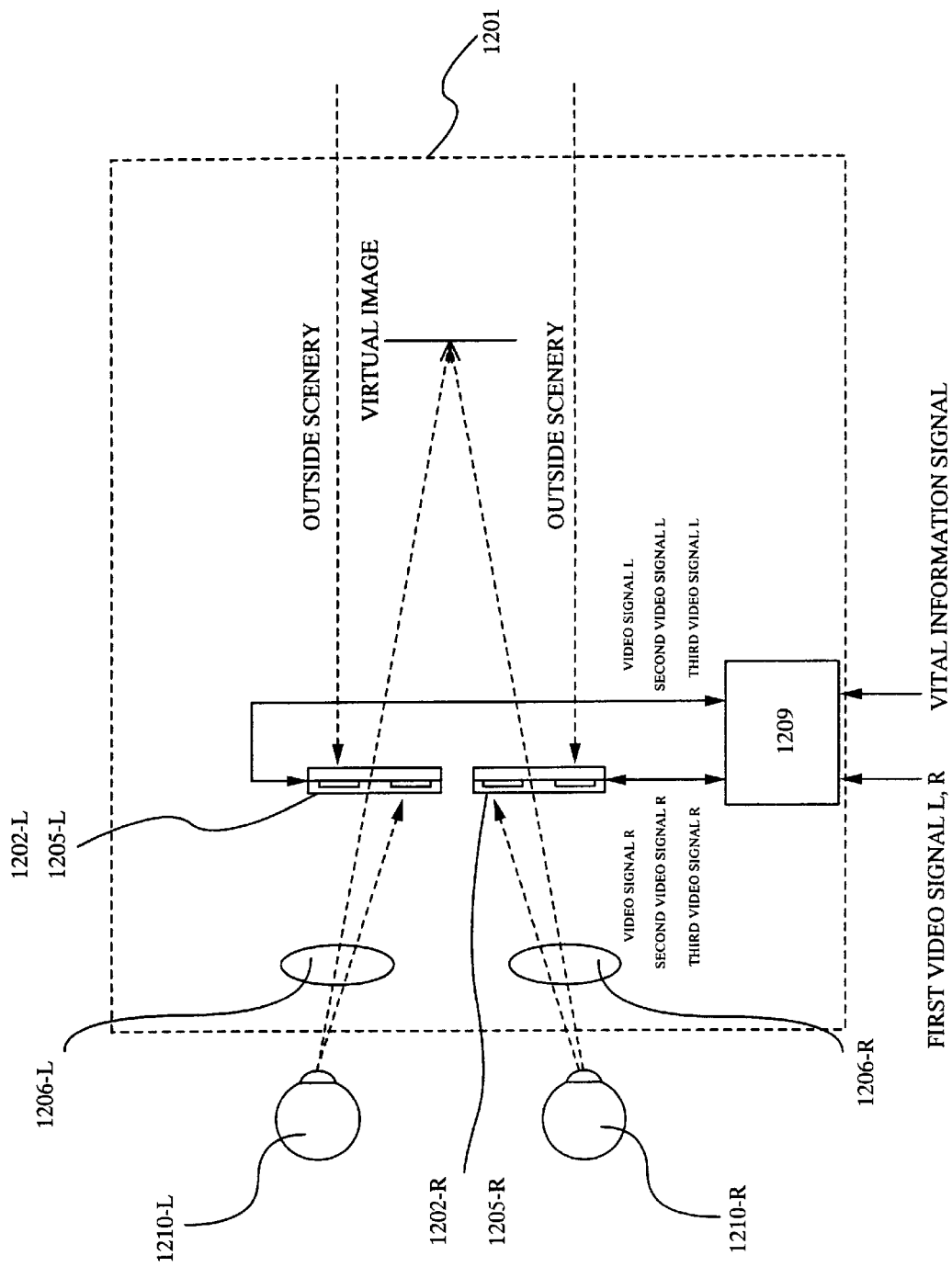
FIG. 12 is a view showing the schematic construction of a goggle type display device system according to Embodiment 6 of the present invention.

FIG. 12 is a schematic constructional view showing a goggle type display device system of this embodiment. Reference symbol 1201 denotes a goggle type display device and 1202-L, 1202-R denote LCD panels with built-in image sensors. The image sensors incorporated in these LCD panels 1202-L, 1202-R convert images of user's eyes into third video signals L, R and take outside scenery (images) to convert it into a second video signal L and a second video signal R. Reference symbols 1205-L, 1205-L denote LED back lights each having a photoconductive plate 1203 (not shown) and an LED 1204 (not shown). Lenses are designated by 1206-L and 1206-R. Reference symbol 1209 denotes a video signal control circuit that receives inputs from the external, namely, first video signals from an external device, vital information signals of a user, the second video signal L, second video signal R, third video signal L and third video signal R from the image sensors incorporated in the LCD panels 1202-L, 1202-R. Also, the video signal control circuit 1209 provides the LCD panels 1202-L, 1202-R with a video signal L and a video signal R, respectively.

The goggle type display system of this embodiment comprises, other than these components, a sensor for obtaining user's vital information to convert it into the vital information signal, speakers or headphones for outputting voice or music, etc.

Figure 13:
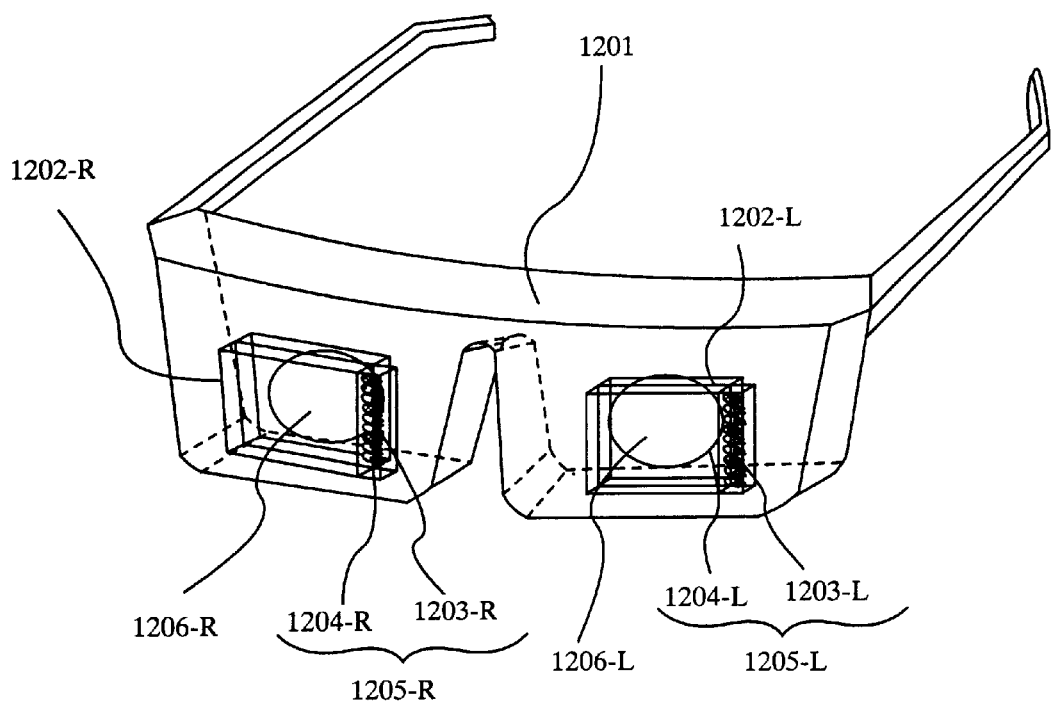
FIG. 13 is a perspective view showing the appearance of the goggle type display device system according to Embodiment 6 of the present invention.

FIG. 13 shows in perspective view the structure of the goggle type display device system of this embodiment shown in FIG. 12.

Any of the above Embodiments 1 to 3 may be referred with regard to the operation of the goggle type display device of this embodiment.

Embodiment 7

Now, a description will be given below on an example of a method for manufacturing the LCD panels used in the above Embodiments 1 to 6. This embodiment shows a case, with reference to FIGS. 16A to 17B, where a plurality of TFTs (thin film transistors) are formed on a substrate having an insulating surface, and an active matrix circuit as a display unit, a source signal line driver circuit, a gate signal line driver circuit, a digital data dividing circuit and other peripheral circuits, etc., which are all together formed on the same single substrate. The example below shows a pixel TFT that is a member constituting the active matrix circuit and a CMOS circuit that is a basic circuit for the other circuits (the source signal line driver circuit, the gate signal line driver circuit and the other peripheral circuit), which are formed simultaneously. The example below gives a description on a manufacturing method of the CMOS circuit in which one gate electrode is provided for each of a p-channel TFT and an n-channel TFT. However, it is also possible to similarly fabricate a CMOS circuit with a TFT that has a plurality of gate electrodes, such as a double gate type TFT or a triple gate type TFT. Though the pixel TFT in the example below is a double gate n-channel TFT, it may be a single gate TFT, a triple gate TFT, etc.

See FIG. 16A to 17B. First, a non-alkaline glass substrate representative of which is, for example, Corning 1737 glass substrate is used for a substrate 7001. On one surface of the substrate 7001 where a TFT is to be formed, a base film 7002 made from silicon oxide is formed to have a thickness of 200 nm. The base film 7002 may be a laminated film formed by layering the silicon oxide film and a silicon nitride film, or may be a single layer of silicon nitride film. Also, the base film 7002 may have a layered structure of a silicon nitride oxide film and a silicon oxide film.

Next, an amorphous silicon film with a thickness of 50 nm is formed on this base film 7002 by plasma CVD. Though depending on hydrogen content of the amorphous silicon film, the film is preferably heated up to 400 to 500° C. for dehydrogenation, reducing the hydrogen content of the amorphous silicon film to 5 atm % or less. Then crystallization step is performed on the dehydrogenated film to form a crystalline silicon film.

This crystallization step may employ a known laser crystallization technique or thermal crystallization technique. In this embodiment, KrF excimer laser light of pulse oscillation type is converged into a linear beam to irradiate the amorphous silicon film, forming the crystalline silicon film.

Used in this embodiment as an initial film is an amorphous silicon film, but a microcrystal silicon film may be used as the initial film. Alternatively, a crystalline silicon film may be directly formed.

The thus formed crystalline silicon film is patterned to form island-like semiconductor active layers 7003, 7004, 7005.

A gate insulating film 7006 containing mainly silicon oxide or silicon nitride is then formed to cover the semiconductor layers 7003, 7004, 7005. A silicon nitride oxide film with a thickness of 100 nm is formed here by plasma CVD. Though not shown in FIGS. 16A to 16E, formed on the surface of the gate insulating film 7006 by sputtering are: a tantalum (Ta) film as a first conductive film having a thickness of 10 to 200 nm, for example, 50 nm; and an aluminum (Al) film as a second conductive film having a thickness of 100 to 1000 nm, for example, 200 nm, the first and second conductive films constituting a first gate electrode. Applying a known patterning technique, first conductive films 7007, 7008, 7009, 7010 and second conductive films 7012, 7013, 7014, 7015 which constitute first gate electrodes are formed.

When aluminum is used for the second conductive film that is a constituent of the first gate electrode, pure aluminum as well as an aluminum alloy added with a 0.1 to 5 atm % of element selected from titanium, silicon and scandium may be used. When copper is used instead, though not shown, it is preferable to form a silicon nitride film on the surface of the gate insulating film 7006.

The structure in FIGS. 16A to 16E includes a holding capacitance portion arranged on the drain side of the n-channel TFT that constitutes the pixel matrix circuit. At this time, wiring electrodes 7011, 7016 of the holding capacitance portion are formed from the same material that is used to form the first gate electrode.

Figure 16A:
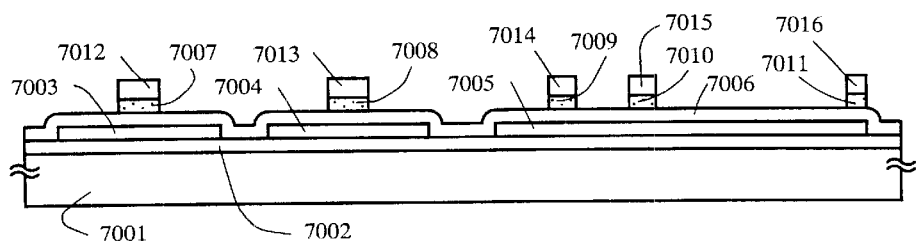
FIGS. 16A to 16E are views showing an example of a manufacturing process of an LCD panel for use in a goggle type display device system of Embodiment 7 of the present invention.

After the structure shown in FIG. 16A is formed in this way, doping step with n-type dopant is performed for the first time. As an impurity element for imparting n-type to a crystalline semiconductor material, phosphorous (P), arsenic (As), antimony (Sb), etc. are known. Here, phosphorous is used and ion doping is carried out employing phosphine ($PH_3$). In this step, the acceleration voltage is set to a rather high value of 80 keV with the intention of doping through the gate insulating film 7006 the semiconductor layer lying below there with phosphorous. The doped region thus formed are to form first doped regions 7034, 7042, 7046 of the n-channel TFT which are shown later and serves as an LDD region. Accordingly, phosphorous concentration in this region is preferably within a range between $1\times10^{16}$ atms/$cm^3$ and $1\times10^{19}$ atms/$cm^3$, and is set to $1\times10^{18}$ atms/$cm^3$ here.

The impurity element added in the semiconductor active layer needs to be activated by laser annealing or heat treatment. Although this step may be performed after a doping step for forming source and drain regions, to activate the element by laser annealing at this stage is very effective.

Figure 16B:
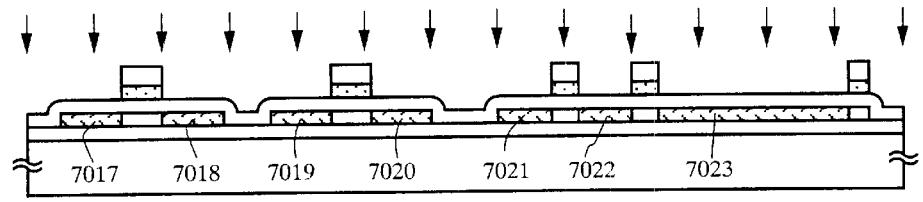

The first conductive films 7007, 7008, 7009, 7010 and second conductive films 7012, 7013, 7014, 7015 which constitute the first gate electrodes function as masks against phosphorous doping in this step. As a result, regions of the semiconductor layer beneath the first gate electrodes, the layer itself lying below the gate insulating film, are doped with absolutely or almost no phosphorous. Thus, as shown in FIG. 16B, lightly doped regions 7017, 7018, 7019, 7020, 7021, 7022, 7023 which are doped with phosphorous are formed.

Figure 16C:
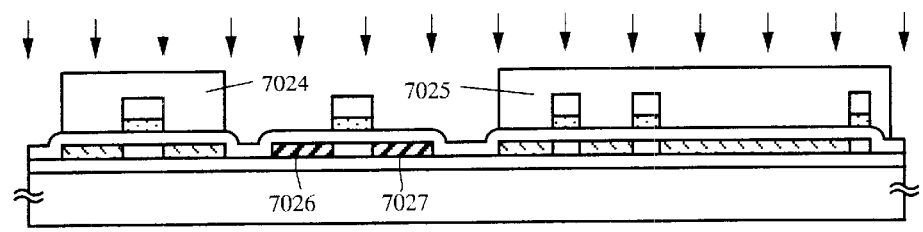

Next, while using a photoresist film as a mask and covering regions for forming the n-channel TFTs with resist masks 7024, 7025, doping step to impart p-type is performed only on regions for forming the p-channel TFT. As an impurity element for imparting p-type, boron (B), aluminum (Al) and gallium (Ga) are known. Here, boron is chosen as the impurity element and is added by ion doping using dibolane ($B_2H_6$). The acceleration voltage here is also 80 keV, and the regions are doped with boron in a concentration of $2\times10^{20}$ atms/$cm^3$. Thus, as shown in FIG. 16C, regions 7026, 7027 doped with a high concentration of boron are formed. The regions will become source and drain regions of the p-channel TFT.

After removing the resist masks 7024, 7025, a step of forming second gate electrodes is performed. Here, tantalum (Ta) is used for a material of the second gate electrodes and a Ta film is formed to have a thickness of 100 to 1000 nm, for example, 200 nm. The film is patterned by a known technique to form second gate electrodes 7028, 7029, 7030, 7031. The patterning at this time is made in such a way that each second gate electrode has a length of 5 $\mu$m. As a result, each second gate electrode has on each side of the first gate electrode a region that is in contact with the gate insulating film and that has a length of 1.5 $\mu$m.

The holding capacitance portion arranged on the drain side of the n-channel TFT that constitutes the pixel matrix circuit has an electrode 7032. The electrode 7032 and the second gate electrodes are formed simultaneously.

Then, using as masks the second gate electrodes 7028, 7029, 7030, 7031, a doping step with an impurity element for imparting n-type is performed for the second time. As in the first time, ion doping with the use of phosphine ($PH_3$) is employed. In this step also, a rather high acceleration voltage of 80 keV is set in order to dope through the gate insulating film 7006 the semiconductor layer lying below there with phosphorous. The regions doped with phosphorous here function in the n-channel TFTs as source regions 7035, 7043 and drain regions 7036, 7047. The phosphorous concentration in the regions is therefore preferably set to $1\times10^{19}$ to $1\times10^{21}$ atms/$cm^3$, here, $1\times10^{20}$ atms/$cm^3$.

Though not illustrated here, a part of the gate insulating film which covers the source regions 7035, 7043 and the drain regions 7036, 7047 may be removed so that the semiconductor layer areas corresponding to those regions are exposed and directly doped with phosphorous. If this step is added, the acceleration voltage in the ion doping can be reduced to 10 keV, and phosphorous doping can be efficiently carried out.

A source region 7039 and drain region 7040 of the p-channel TFT are doped with the same concentration of phosphorous. However, the regions are doped at the preceding step with boron in a concentration twice the phosphorous concentration concerned. Therefore, the conductivity thereof is not inverted, causing no problem in the operation of the p-channel TFT.

The impurity elements added in respective concentrations to impart n-type or p-type are not active by themselves and do not work effectively, requiring activation step. This step may employ thermal annealing with the use of an electric heating furnace, laser annealing with the use of the above-mentioned excimer laser, or rapid thermal annealing (RTA) with the use of a halogen lamp.

In thermal annealing, activation is made by a heat treatment in nitrogen atmosphere at 550° C. for 2 hours. The second conductive film constituting the first gate electrodes uses aluminum in this embodiment. The aluminum atoms are prevented from diffusing through other regions by a blocking layer of tantalum that forms the first conductive film and the second gate electrodes both of which cover the aluminum. In laser annealing, activation is made by lineally converging and irradiating KrF excimer laser light of pulse oscillation type. If thermal annealing is carried out following laser annealing, even better result is obtained. This step also has an effect of annealing regions with damaged crystallinity from ion doping, improving the crystallinity of the regions.

Formed up through the above step are the gate electrodes consisting of the first gate electrodes and the second gate electrodes that cover the first gate electrodes, and the source region and the drain region on each side of the respective second gate electrodes in the n-channel TFT. Also formed in a self-alignment manner is the structure in which the first doped region arranged in the semiconductor layer overlaps through the gate insulating film and the region of the second gate electrode which is in contact with the gate insulating film. On the other hand, in the p-channel TFT, a part of the source region and a part of the drain region overlap with the second gate electrode, which brings about no problem in practical use.

Figure 16D:
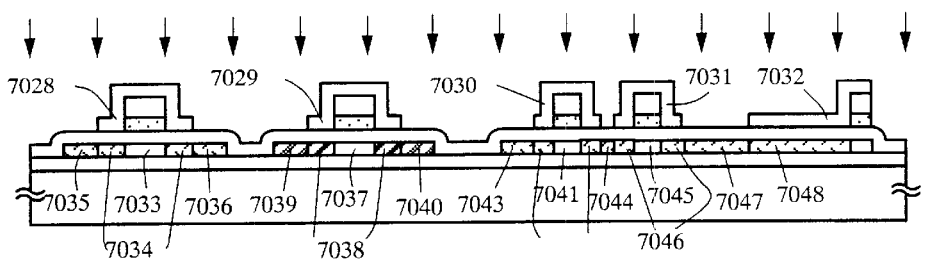

Upon obtaining the state of FIG. 16D, a first interlayer insulating film 7049 is formed to have a thickness of 1000 nm. As the first interlayer insulating film 7049, a silicon oxide film, a silicon nitride film, a silicon oxide nitride film, an organic resin film and a laminated film of those may be used. This embodiment employs, though not shown, a two-layer structure in which a silicon nitride film with a thickness of 50 nm is first formed and a silicon oxide film with a thickness of 950 nm is further formed.

The first interlayer insulating film 7049 is thereafter patterned to form contact holes in the source regions and drain regions of the respective TFTs. Then, source electrodes 7050, 7052, 7053 and drain electrodes 7051, 7054 are formed. These electrodes in this embodiment, though not shown, are formed by patterning a three-layer structure film with a 100 nm titanium film, a 300 nm aluminum film including titanium and a 150 nm titanium film which are sequentially formed by sputtering.

Figure 16E:
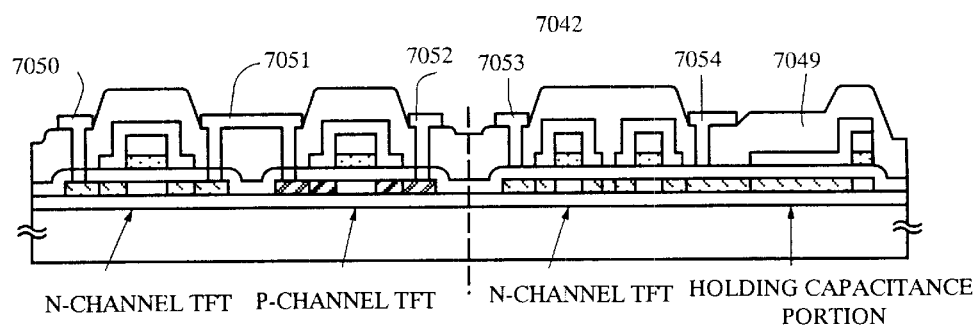

As shown in FIG. 16E, a CMOS circuit and an active matrix circuit are thus formed on the substrate 7001. The holding capacitance portion is simultaneously formed on the drain side of the n-channel TFT in the active matrix circuit. An active matrix substrate reaches completion as above.

Subsequently, a description will be made with reference to FIGS. 17A and 17B on a process of manufacturing an LCD panel, based on the CMOS circuit and the active matrix circuit which are formed on the same substrate through the above steps. First, on the substrate in the state of FIG. 16E, a passivation film 7055 is formed to cover the source electrodes 7050, 7052, 7053, the drain electrodes 7051, 7054 and the first interlayer insulating film 7049. The passivation film 7055 is made of a silicon nitride film having a thickness of 50 nm. A second interlayer insulating film 7056 made of an organic resin film is further formed to have a thickness of about 1000 nm. Usable organic resin film includes a polyimide film, an acryl film and a polyimideamide film. Enumerated as advantages in using the organic resin film are: simple film formation method; a reduced parasitic capacitance owing to low relative permittivity; and excellency in flatness. Other organic resin films than the ones mentioned above may also be used. Here, polyimide of the type to be thermally polymerized after applied to the substrate is used and burning at a temperature of 300° C. follows to finish the film.

A light shielding layer 7057 is next formed on a part of a pixel region of the second interlayer insulating film 7056. The light shielding layer 7057 may be made of a metal film or an organic resin film with pigment contained therein. Here, a titanium film is formed by sputtering.

After forming the light shielding layer 7057, a third interlayer insulating film 7058 is formed. This third interlayer insulating film 7058 is formed, as is the second interlayer insulating film 7056, using an organic resin film. A contact hole reaching the drain electrode 7054 is formed through the second interlayer insulating film 7056 and the third interlayer insulating film 7058 to form a pixel electrode 7059. The pixel electrode 7059 uses a transparent conductive film if a transmission type liquid crystal display device is aimed, and a metal film is used if a reflection type liquid crystal display device is to be made. Here, to fabricate a transparent type liquid crystal display device, an indium tin oxide (ITO) film with a thickness of 100 nm is formed by sputtering, forming the pixel electrode 7059.

Figure 17A:
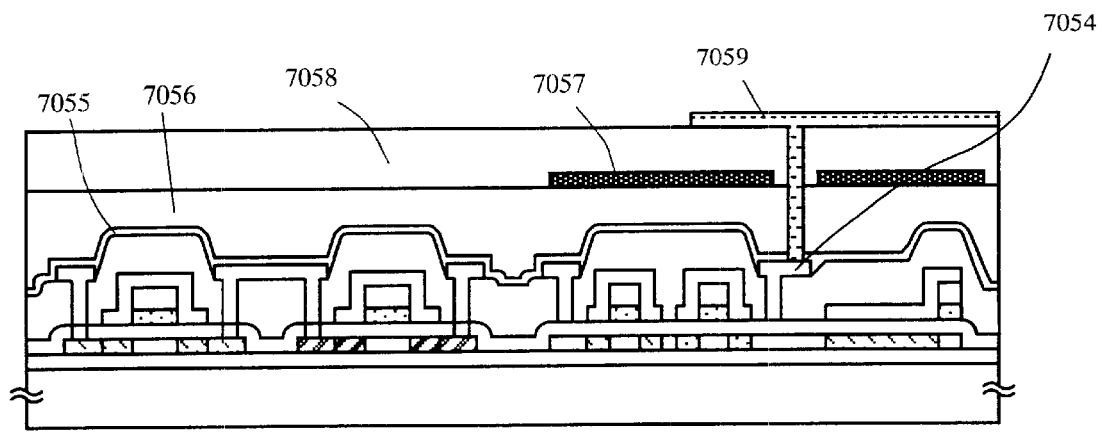
FIGS. 17A and 17B are views showing the example of the manufacturing process of the LCD panel for use in a goggle type display device system of Embodiment 7 of the present invention.
Figure 17B:
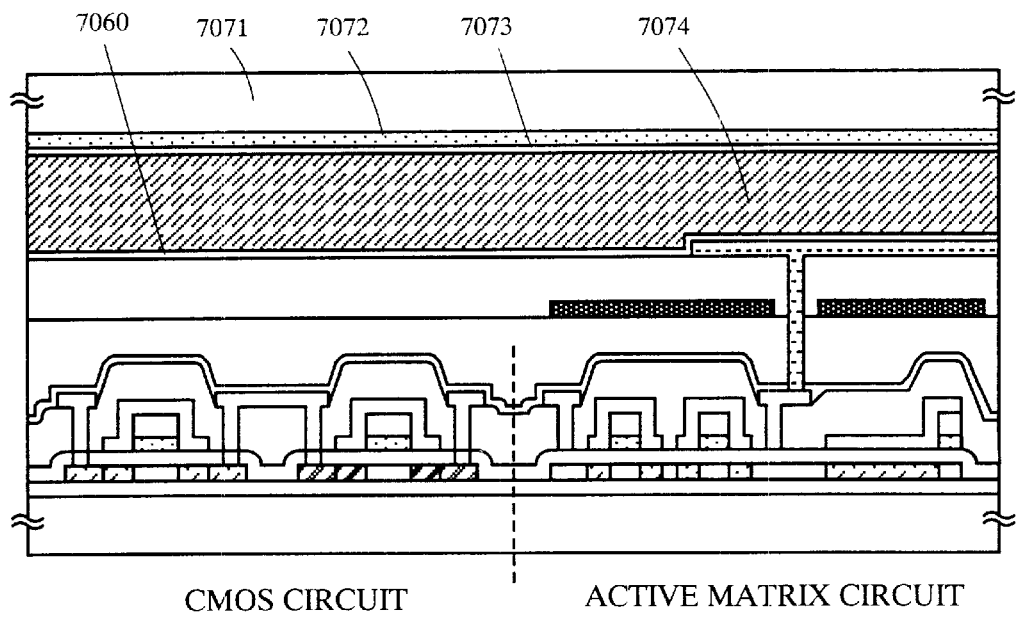

When the state of FIG. 17A is obtained, an orientated film 7060 is formed. Normally, orientated films for liquid crystal display elements often use polyimide resins. An opposite side substrate 7071 has an opposite electrode 7072 and an orientated film 7073 which are formed thereon. After formation, the orientated film is subjected to a rubbing treatment so that liquid crystal molecules are oriented in parallel with a certain pre-tilt angle.

Through the steps above, the substrate on which the active matrix circuit and the CMOS circuit are formed and the opposite substrate are bonded to each other by a known cell assembling process with a sealant and a spacer (both of which are not shown) interposed therebetween. Thereafter, a liquid crystal material 7074 is injected between the substrates and an end sealing material (not shown) completely seals the substrates. Thus, the LCD panel shown in FIG. 17B is finished.

Embodiment 8

For the above liquid crystal display devices of the present invention, various kinds of liquid crystal may be used other than nematic liquid crystal. For example, usable liquid crystal includes ones disclosed in: 1998, SID, "Characteristics and Driving Scheme of Polymer-Stabilized Monostable FLCD Exhibiting Fast Response Time and High Contrast Ratio with Gray-Scale Capability" by H. Furue et al.; 1997, SID DIGEST, 841, "A Full-Color Thresholdless Antiferroelectric LCD Exhibiting Wide Viewing Angle with Fast Response Time" by T. Yoshida et al.; 1996, J. Mater. Chem. 6(4), 671–673, "Thresholdless Antiferroelectricity in Liquid Crystals and its Application to Displays" by S. Inui et al.; and U.S. Pat. No. 5594569.

Figure 25:
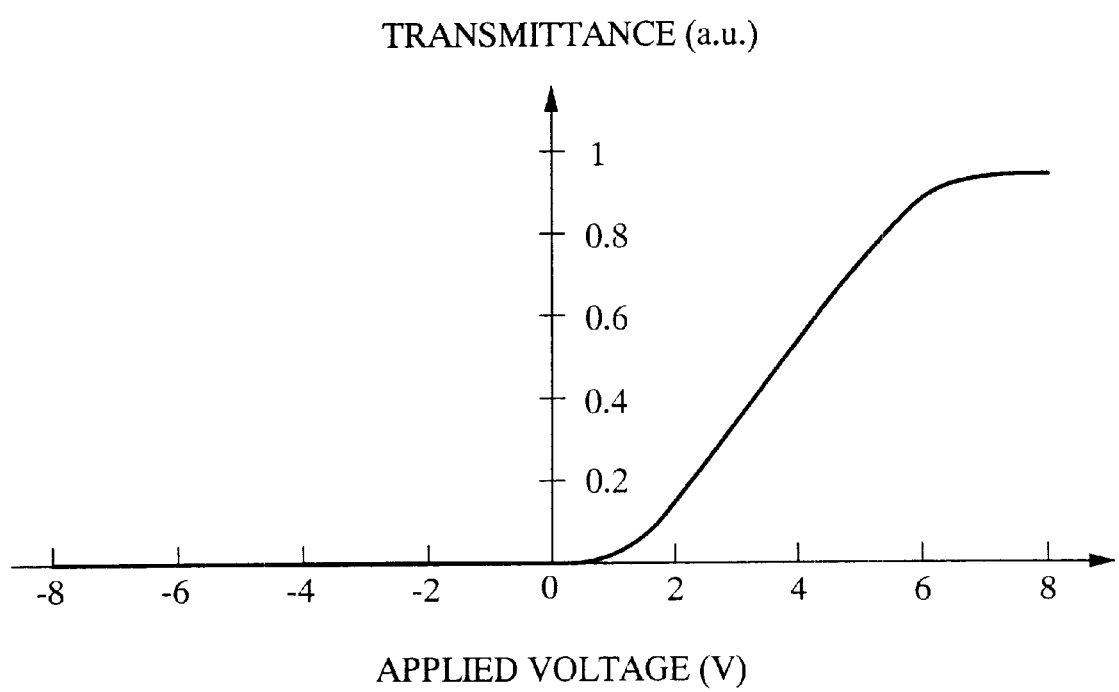
FIG. 25 is a diagram showing the electro-optical characteristic of monostable FLC according to Embodiment 8 of the present invention.

FIG. 25 shows electro-optical characteristic of a monostable FLC (Ferroelectric Liquid Crystal). The FLC is prepared such that transition between cholesteric phase and chiral smectic phase is caused while applying DC voltage on FLC that exhibits transition system between isotropic phase, cholesteric phase and chiral smectic phase, and then, corn edges are aligned substantially in a rubbing direction. The display mode by ferroelectric liquid crystal as shown in FIG. 25 is called "Half-letter V switching mode". In the graph shown in FIG. 25, the axis of the ordinate indicates transmittance (arbitrary unit) and the axis of abscissa indicates applied voltage. Detailed descriptions on the "Half-letter V switching mode" is found in Terada et al. "Half-letter V Switching Mode FLCD", Extended Abstracts for The 46th Meeting of The Japan Society of Applied Physics and Related Societies, p. 1316, [Mar. 1999], and Yoshihara et al. "Time Division Full-Color LCD using Ferroelectric Liquid Crystal", Liquid Crystal (Ekisho), vol. 3 (no. 3), p. 190.

As shown in FIG. 25, it can be understood that using such ferroelectric mixed liquid crystal makes possible the low-voltage driving and gradation display. The liquid crystal display devices of the present invention may use also ferroelectric liquid crystal that shows such electro-optical characteristic.

Liquid crystal that exhibits antiferroelectric phase in a certain temperature range is called antiferroelectric liquid crystal (AFLC). Among mixed liquid crystal having antiferroelectric liquid crystal, there is one called thresholdless-antiferroelectric mixed liquid crystal, which exhibits electro-optical response characteristic in that the transmittance varies continuously with respect to the electric field. Some of the thresholdless-antiferroelectric mixed liquid crystal show electro-optical response characteristic of so-called letter V shape, and there has been found among them ones the driving voltage of which is about +2.5 V (cell thickness of about 1 µm to 2 µm).

In general, thresholdless-antiferroelectric mixed liquid crystal is large in spontaneous polarization and dielectric permittivity of liquid crystal itself is high. For that reason, a relatively large holding capacitance is required for a pixel when using for a liquid crystal display device the thresholdless-antiferroelectric mixed liquid crystal. Thus, preferably used is thresholdless-antiferroelectric mixed liquid crystal that is small in spontaneous polarization.

To use such thresholdless-antiferroelectric mixed liquid crystal for the liquid crystal display devices of the present invention realizes the low-voltage driving, thereby realizing lowered power consumption.

Embodiment 9

This embodiment demonstrates a process for producing an EL (electroluminescence) display device as a display of the goggle type display system of the present invention.

Figure 19A:
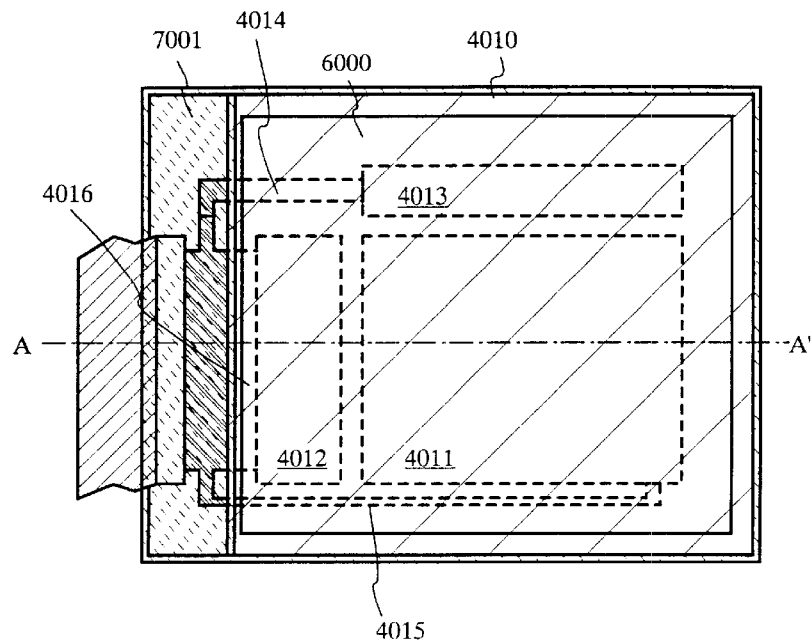
FIGS. 19A and 19B are views showing a structure of an EL display device of Embodiment 9 of the present invention.

FIG. 19A is a top view showing an EL display device, which was produced according to Embodiment 9 of the present application. In FIG. 19A, there are shown a substrate 4010, a pixel portion 4011, a source side driving circuit portion 4012, and a gate side driving circuit portion 4013, each driving circuit connecting to wirings 4014–4016 which reach FPC 4017 leading to external equipment.

Figure 19B:
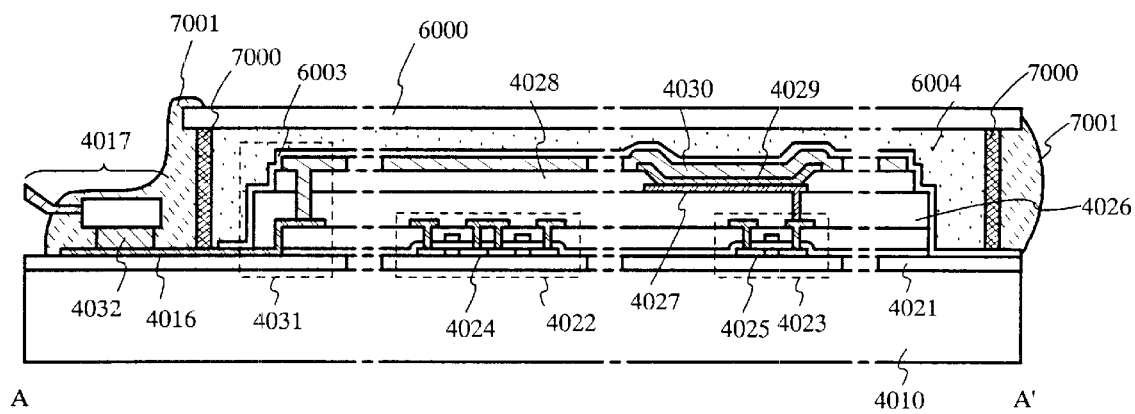

FIG. 19B is a sectional view showing the structure of the EL display device in this embodiment. The pixel portion, preferably together with the driving circuit portion, is enclosed by a covering material 6000, a sealing material (or housing material) 7000, and an end-sealing material (or second sealing material) 7001.

Furthermore, there is shown a substrate 4010, a base film 4021, a TFT 4022 for the driving circuit portion, and a TFT 4023 for the pixel portion. The TFT 4022 shown is a CMOS circuit consisting of an n-channel type TFT and a p-channel type TFT. The TFT 4023 shown is the one, which controls current to the EL element.

Upon completion of TFT 4022 (for the driving circuit portion) and TFT 4023 (for the pixel portion), a pixel electrode 4027 is formed on the interlayer insulating film (planarizing film) 4026 made of a resin. This pixel electrode is a transparent conductive film, which is electrically connected to the drain of TFT 4023 for the pixel portion. The transparent conductive film may be formed from a compound (called ITO) of indium oxide and tin oxide or a compound of indium oxide and zinc oxide. On the pixel electrode 4027 is formed an insulating film 4028, in which is formed an opening above the pixel electrode 4027.

Subsequently, the EL layer 4029 is formed. It may be of single-layer structure or multi-layer structure by freely combining known EL materials such as an injection layer, a hole transport layer, a light emitting layer, an electron transport layer, and an electron injection layer. Any known technology may be available for such structure. The EL material is either a low-molecular material or a high-molecular material (polymer). The former may be applied by vapor deposition, and the latter may be applied by a simple method such as spin coating, printing, or ink-jet method.

In this example, the EL layer is formed by vapor deposition through a shadow mask. The resulting EL layer permits each pixel to emit light differing in wavelength (a red emitting layer, a green emitting layer, and a blue emitting layer). This realizes the color display. Alternative systems available include the combination of color conversion layer (CCM) and color filter and the combination of white light emitting layer and color filter. Needless to say, the EL display device may be monochromatic.

On the EL layer 4029 is formed a cathode 4030. Prior to this step, it is desirable to clear moisture and oxygen as much as possible from the interface between the EL layer 4029 and the cathode 4030. This object may be achieved by forming the EL layer 4029 and the cathode 4030 consecutively in a vacuum, or by forming the EL layer 4029 in an inert atmosphere and then forming the cathode 4030 in the same atmosphere without admitting air into it. In this Example, the desired film was formed by using a film-forming apparatus of a multi-chamber system (cluster tool system).

The multi-layer structure composed of a lithium fluoride film and an aluminum film is used in this Embodiment as the cathode 4030. To be concrete, the EL layer 4029 is coated by vapor deposition with a lithium fluoride film (1 nm thick) and an aluminum film (300 nm thick) sequentially. Needless to say, the cathode 4030 may be formed from MgAg electrode which is a known cathode material. Subsequently, the cathode 4030 is connected to a wiring 4016 in the region indicated by 4031. The wiring 4016 to supply a prescribed voltage to the cathode 4030 is connected to the FPC 4017 through an electrically conductive paste material 4032.

The electrical connection between the cathode 4030 and the wiring 4016 in the region 4031 needs contact holes in the interlayer insulating film 4026 and the insulating film 4028. These contact holes may be formed when the interlayer insulating film 4026 undergoes etching to form the contact hole for the pixel electrode or when the insulating film 4028 undergoes etching to form the opening before the EL layer is formed. When the insulating film 4028 undergoes etching, the interlayer insulating film 4026 may be etched simultaneously. Contact holes of good shape may be formed if the interlayer insulating film 4026 and the insulating film 4028 are made of the same material.

Then, a passivation film 6003, a filling material 6004 and a covering material 6000 are formed so that these layers cover the EL element.

Furthermore, the sealing material 7000 is formed inside of the covering material 6000 and the substrate 4010 such as surrounding the EL element, and the end-sealing material (second sealing material) 7001 is formed outside of the sealing material 7000.

The filling material 6004 is formed to cover the EL element and also functions as an adhesive to adhere to the covering material 6000. As the filling material 6004, PVC (polyvinyl chloride), an epoxy resin, a silicon resin, PVB (polyvinyl butyral), or EVA (ethylenvinyl acetate) can be utilized. It is preferable to form a desiccant in the filling material 6004, since a moisture absorption can be maintained.

Also, spacers can be contained in the filling material 6004. It is preferable to use spherical spacers comprising barium oxide to maintain the moisture absorption in the spacers.

In the case of that the spaces are contained in the filling material, the passivation film 6003 can relieve the pressure of the spacers. Of course, the other film different from the passivation film, such as an organic resin, can be used for relieving the pressure of the spacers.

As the covering material 6000, a glass plate, an aluminum plate, a stainless plate, a FRP (Fiberglass-Reinforced Plastics) plate, a PVF (polyvinyl fluoride) film, a Mylar film, a polyester film or an acryl film can be used. In a case that PVB or EVA is employed as the filling material 6004, it is preferable to use an aluminum foil with a thickness of some tens of m sandwiched by a PVF film or a Mylar film.

It is noted that the covering material 6000 should have a light transparency with accordance to a light emitting direction (a light radiation direction) from the EL element.

The wiring 4016 is electrically connected to FPC 4017 through the gap between the sealing material 7000 and the end-sealing material 7001, and the substrate 4010. As in the wiring 4016 explained above, other wirings 4014 and 4015 are also electrically connected to FPC 4017 under the sealing material 4018.

Embodiment 10

Figure 20A:
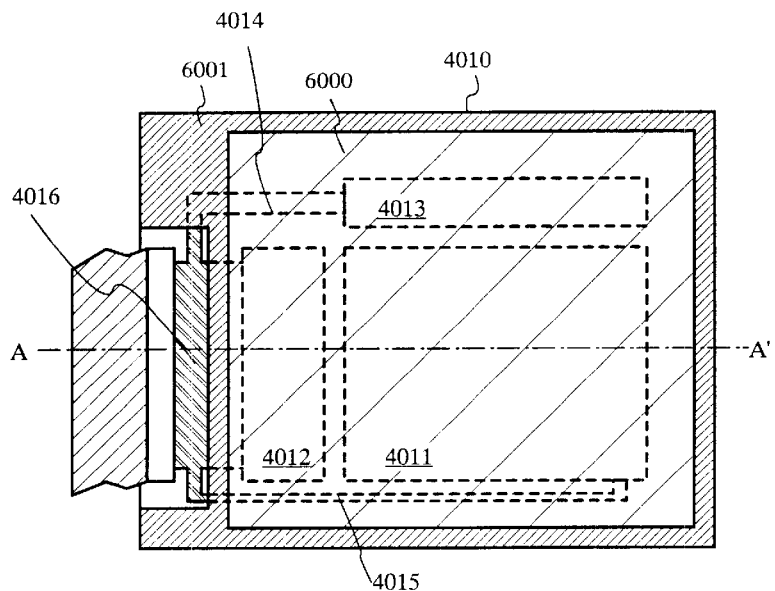
FIGS. 20A and 20B are views showing a structure of an EL display device of Embodiment 10 of the present invention.
Figure 20B:
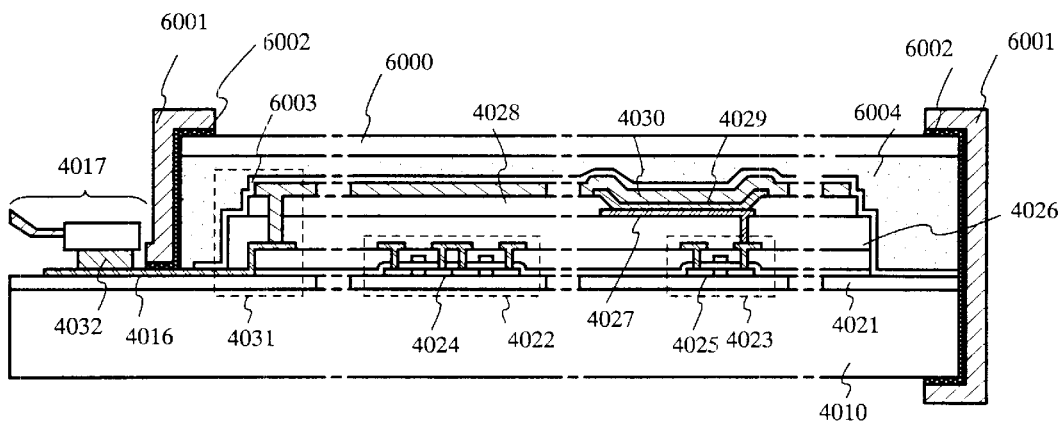

In this embodiment, another EL display device having a different structure from Embodiment 9 is explained, as shown in FIGS. 20A and 20B. The same reference numerals in FIG. 20A and 20B as in FIGS. 19A and 19B indicate same constitutive elements, so an explanation is omitted.

FIG. 20A shows a top view of the EL module in this embodiment and FIG. 20B shows a sectional view of A–A' of FIG. 20A.

According to Embodiment 9, the passivation film 6003 is formed to cover a surface of the EL element.

The filling material 6004 is formed to cover the EL element and also functions as an adhesive to adhere to the covering material 6000. As the filling material 6004, PVC (polyvinyl chloride), an epoxy resin, a silicon resin, PVB (polyvinyl butyral), or EVA (ethylenvinyl acetate) can be utilized. It is preferable to form a desiccant in the filling material 6004, since a moisture absorption can be maintained.

Also, spacers can be contained in the filling material 6004. It is preferable to use spherical spacers comprising barium oxide to maintain the moisture absorption in the spacers.

In the case of that the spaces are contained in the filling material, the passivation film 6003 can relieve the pressure of the spacers. Of course, the other film different from the passivation film, such as an organic resin, can be used for relieving the pressure of the spacers.

As the covering material 6000, a glass plate, an aluminum plate, a stainless plate, a FRP (Fiberglass-Reinforced Plastics) plate, a PVF (polyvinyl fluoride) film, a Mylar film, a polyester film or an acryl film can be used. In a case that PVB or EVA is employed as the filling material 6004, it is preferable to use an aluminum foil with a thickness of some tens of m sandwiched by a PVF film or a Mylar film.

It is noted that the covering material 6000 should have a light transparency with accordance to a light emitting direction (a light radiation direction) from the EL element.

Next, the covering material 6000 is adhered using the filling material 6004. Then, the flame material 6001 is attached to cover side portions (exposed faces) of the filling material 6004. The flame material 6001 is adhered by the sealing material (acts as an adhesive) 6002. As the sealing material 6002, a light curable resin is preferable. Also, a thermal curable resin can be employed if a heat resistance of the EL layer is admitted. It is preferable for the sealing material 6002 not to pass moisture and oxygen. In addition, it is possible to add a desiccant inside the sealing material 6002.

The wiring 4016 is electrically connected to FPC 4017 through the gap between the sealing material 6002 and the substrate 4010. As in the wiring 4016 explained above, other wirings 4014 and 4015 are also electrically connected to FPC 4017 under the sealing material 6002.

Embodiment 11

Figure 21:
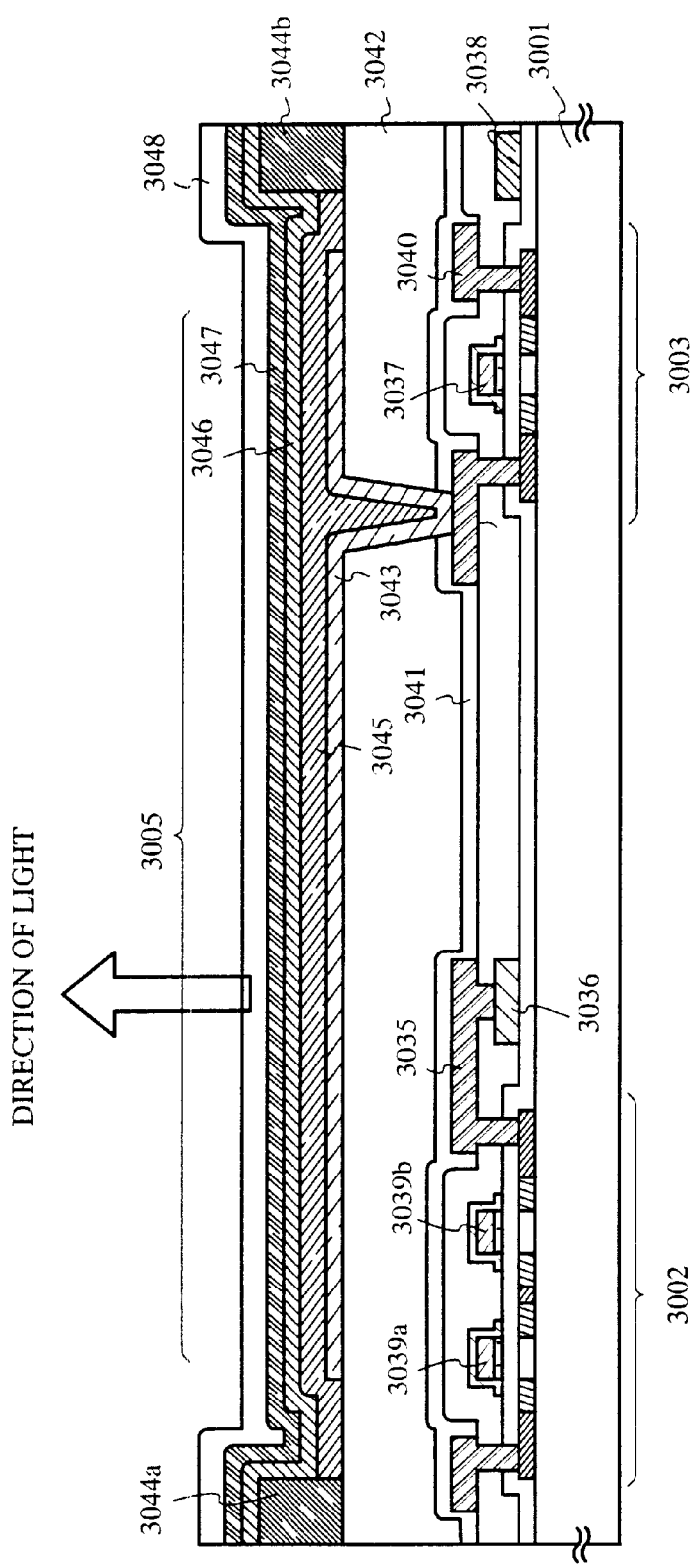
FIG. 21 is a view showing a cross section of a pixel portion in the an EL display device of Embodiment 11 of the present invention.
Figure 22A:
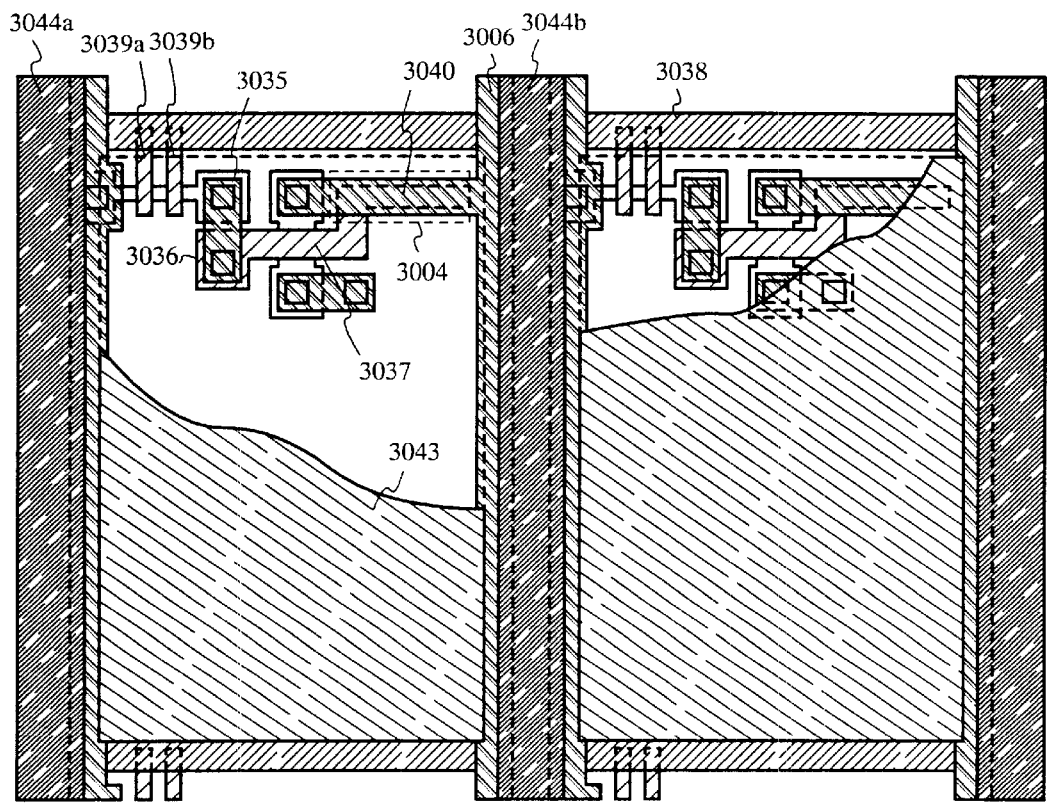
FIGS. 22A and 22B are views showing a structure of the pixel portion in an EL display panel and a circuit structure for the pixel portion, respectively, of Embodiment 11 of the present invention.
Figure 22B:
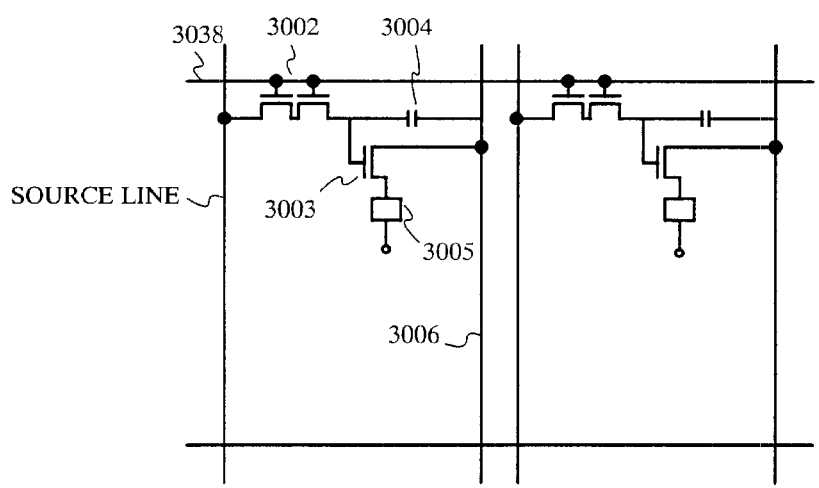

In this embodiment, the structure of the pixel portion in the panel is illustrated in more detail. FIG. 21 shows the cross section of the pixel portion; FIG. 22A shows the top view thereof; and FIG. 22B shows the circuit pattern for the pixel portion. In FIG. 21, FIG. 22A and FIG. 22B, the same reference numerals are referred to for the same numerals, as being common thereto.

In FIG. 21, the switching TFT 3002 formed on the substrate 3001 can have a TFT structure described in Embodiment 7 of the present invention or a conventional TFT structure. In this Embodiment 11, it has a double-gate structure, but its structure and fabrication process do not so much differ from the structures and the fabrication processes illustrated hereinabove, and their description is omitted herein. However, the double-gate structure of the switching TFT 3002 has substantially two TFTs as connected in series, and therefore has the advantage of reducing the off-current to pass therethrough. In this Embodiment, the switching TFT 3002 has such a double-gate structure, but is not limitative. It may have a single-gate structure or a triple-gate structure, or even any other multi-gate structure having more than three gates.

The current-control TFT 3003 is an NTFT (n-channel TFT). The drain wiring 3035 in the switching TFT 3002 is electrically connected with the gate electrode 3037 in the current-control TFT, via the wiring 3036 therebetween. The wiring indicated by 3038 is a gate wiring for electrically connecting the gate electrodes 3039a and 3039b in the switching TFT 3002.

The current-control TFT is a unit for controlling the quantity of current that passes through the EL device. Therefore, a large quantity of current passes through it, and the unit, current-control TFT has a high risk of thermal degradation and degradation with hot carriers. To this unit, therefore, the structure of the invention is favorable, in which an LDD region is so constructed that the gate electrode overlaps with the drain area in the current-control TFT, via a gate-insulating film therebetween.

In this embodiment, the current-control TFT 3003 is illustrated to have a single-gate structure, but it may have a multi-gate structure with a plurality of TFTs connected in series. In addition, a plurality of TFTs may be connected in parallel so that the channel-forming region is substantially divided into plural sections. In the structure of that type, heat radiation can be effected efficiently. The structure is advantageous for protecting the device with it from thermal deterioration.

As in FIG. 22A, the wiring to be the gate electrode 3037 in the current-control TFT 3003 overlaps with the drain wiring 3040 therein in the region indicated by 3004, via an insulating film therebetween. In this state, the region indicated by 3004 forms a capacitor. The capacitor 3004 functions to retain the voltage applied to the gate in the current-control TFT 3003. The drain wiring 3040 is connected with the current supply line (power line) 3006, from which a constant voltage is all the time applied to the drain wiring 3040.

On the switching TFT 3002 and the current-control TFT 3003, formed is a first passivation film 3041. On the first passivation film 3041, formed is a planarizing film 3042 of an insulating resin. It is extremely important that the difference in level of the layered parts in TFT is removed through leveling with the planarizing film 3042. This is because the EL layer to be formed on the previously formed layers in the later step is extremely thin, and if there exist a difference in level of the previously formed layers, the EL device will be often troubled by light emission failure. Accordingly, it is desirable to previously level as much as possible the previously formed layers before the formation of the pixel electrode thereon so that the EL layer could be formed on the leveled surface.

The reference numeral 3043 indicates a pixel electrode (a cathode in the EL device) of a conductive film with high reflectivity. The pixel electrode 3043 is electrically connected with the drain in the current-control TFT 3003. It is preferable that the pixel electrode 3043 is of a low-resistance conductive film of an aluminum alloy, a copper alloy or a silver alloy, or of a laminate of those films. Needless-to-say, the pixel electrode 3043 may have a laminate structure with any other conductive films.

In the recess (this corresponds to the pixel) formed between the banks 3044a and 3044b of an insulating film (preferably of a resin), the light-emitting layer 3045 is formed. In the illustrated structure, only one pixel is shown, but a plurality of light-emitting layers could be separately formed in different pixels, corresponding to different colors of R (red), G (green) and B (blue). The organic EL material for the light-emitting layer may be any -conjugated polymermaterial. Typical polymer materials usable herein include polyparaphenylenevinylene (PVV) materials, polyvinylcarbazole (PVK) materials, polyfluorene materials, etc.

Various types of PVV-type organic EL materials are known, such as those disclosed in "H. Shenk, H. Becker, O. Gelsen, E. Klunge, W. Kreuder, and H. Spreitzer; Polymers for Light Emitting Diodes, Euro Display Proceedings, 1999, pp.33–37" and in Japanese Patent Laid-Open No. 10-92576. Any of such known materials are usable herein.

Concretely, cyanopolyphenylenevinylenes may be used for red-emitting layers; polyphenylenevinylenes may be for green-emitting layers; and polyphenylenevinylenes or polyalkylphenylenes may be for blue-emitting layers. The thickness of the film for the light-emitting layers may fall between 30 and 150 nm (preferably between 40 and 100 nm).

These compounds mentioned above are referred to merely for examples of organic EL materials employable herein and are not limitative at all. The light-emitting layer may be combined with a charge transportation layer or a charge injection layer in any desired manner to form the intended EL layer (this is for light emission and for carrier transfer for light emission).

Specifically, this Embodiment is to demonstrate an example of using polymer materials to form light-emitting layers, which, however, is not limitative. Apart from this, low-molecular organic EL materials may also be used for light-emitting layers. For charge transportation layers and charge injection layers, further employable are inorganic materials such as silicon carbide, etc. Various organic EL materials and inorganic materials for those layers are known, any of which are usable herein.

In this Embodiment, a hole injection layer 3046 of PEDOT (polythiophene) or PAni (polyaniline) is formed on the light-emitting layer 3045 to give a laminate structure for the EL layer. On the hole injection layer 3046, formed is an anode 3047 of a transparent conductive film. In this Embodiment, the light having been emitted by the light-emitting layer 3045 radiates therefrom in the direction toward the top surface (that is, in the upward direction of TFT). Therefore, in this, the anode must transmit light. For the transparent conductive film for the anode, usable are compounds of indium oxide and tin oxide, and compounds of indium oxide and zinc oxide. However, since the anode is formed after the light-emitting layer and the hole injection layer having poor heat resistance have been formed, it is preferable that the transparent conductive film for the anode is of a material capable of being formed into a film at as low as possible temperatures.

When the anode 3047 is formed, the EL device 3005 is finished. The EL device 3005 thus fabricated herein indicates a capacitor comprising the pixel electrode (cathode) 3043, the light-emitting layer 3045, the hole injection layer 3046 and the anode 3047. As in FIG. 22A, the region of the pixel electrode 3043 is nearly the same as the area of the pixel. Therefore, in this, the entire pixel functions as the EL device. Accordingly, the light utility efficiency of the EL device fabricated herein is high, and the device can display bright images.

In this Embodiment, a second passivation film 3048 is formed on the anode 3047. For the second passivation film 3048, preferably used is a silicon nitride film or a silicon oxynitride film. The object of forming the second passivation film 3048 is to insulate the EL device from the outward environment. The film 3048 has the function of preventing the organic EL material from being degraded through oxidation and has the function of preventing it from degassing. With the second passivation film 3048 of that type, the reliability of the EL display device is improved.

As described hereinabove, the EL display panel of the invention fabricated in this Embodiment has a pixel portion for the pixel having the constitution as in FIG. 21, and has the switching TFT through which the off-current to pass is very small to a satisfactory degree, and the current-control TFT resistant to hot carrier injection. Accordingly, the EL display panel fabricated herein has high reliability and can display good images.

Embodiment 12

This Embodiment is to demonstrate a modification of the EL display panel of Embodiment 11, in which the EL device 3005 in the pixel portion has a reversed structure. For this Embodiment, referred to is FIG. 23. The constitution of the EL display panel of this Embodiment differs from that illustrated in FIG. 22A only in the EL device part and the current-control TFT part. Therefore, the description of the other parts except those different parts is omitted herein.

Figure 23:
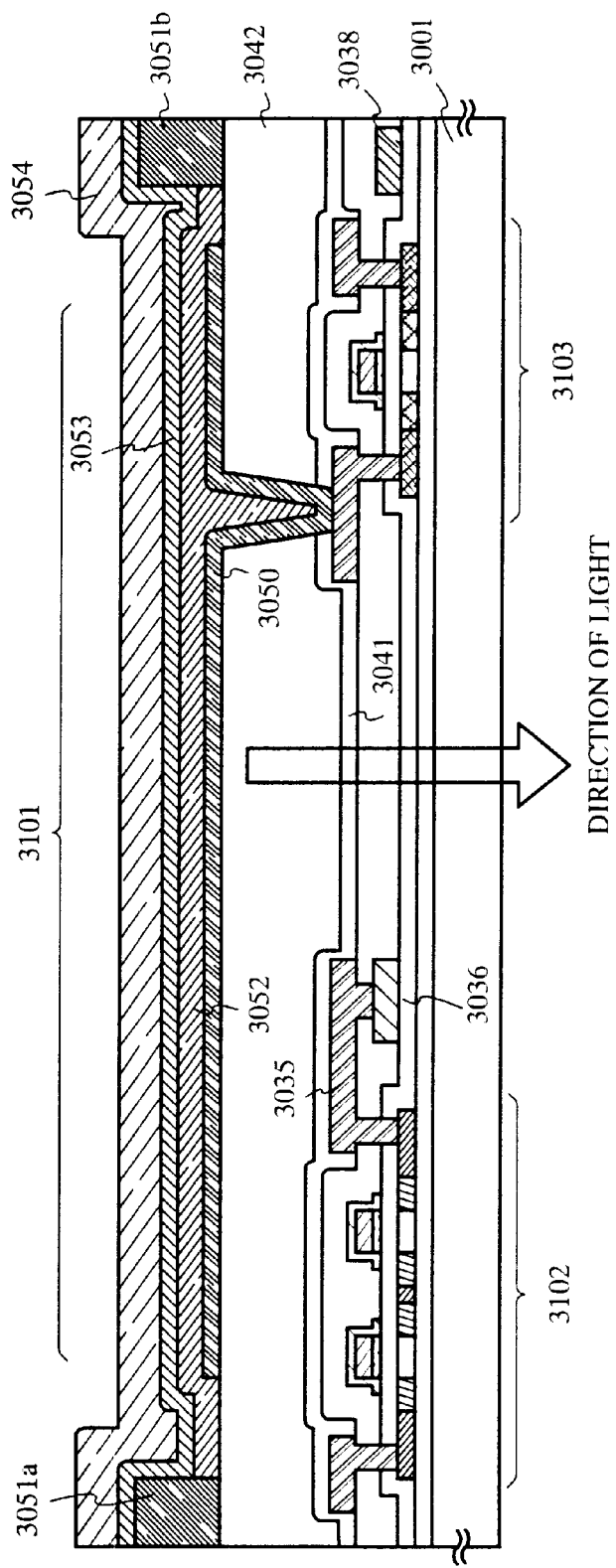
FIG. 23 is a view showing a structure of a pixel portion in an EL display device of Embodiment 12 of the present invention.

In FIG. 23, the current-control TFT 3103 may be a PTFT (p-channel TFT).

In this Embodiment, the pixel electrode (anode) 3050 is of a transparent conductive film. Concretely, used is a conductive film of a compound of indium oxide and zinc oxide. Needless-to-say, also usable is a conductive film of a compound of indium oxide and tin oxide.

After the banks 3051a and 3051b of an insulating film have been formed, a light-emitting layer 3052 of polyvinylcarbazole is formed between them in a solution coating method. On the light-emitting layer 3052, formed are an electron injection layer 3053 of acetylacetonatopotassium, and a cathode 3054 of an aluminum alloy. In this case, the cathode 3054 serves also as a passivation film. Thus is fabricated the EL device 3101.

In this Embodiment, the light having been emitted by the light-emitting layer 3052 radiates in the direction toward the substrate with TFT formed thereon, as in the direction of the arrow illustrated.

Embodiment 13

This Embodiment is to demonstrate modifications of the pixel with the circuit pattern of FIG. 22B. The modifications are as in FIG. 24A to FIG. 24C. In this Embodiment illustrated in those FIG. 24A to FIG. 24C, 3201 indicates the source wiring for the switching TFT 3202; 3203 indicates the gate wiring for the switching TFT 3202; 3204 indicates a current-control TFT; 3205 indicates a capacitor; 3206 and 3208 indicate current supply lines; and 3207 indicates an EL device.

Figure 24A:
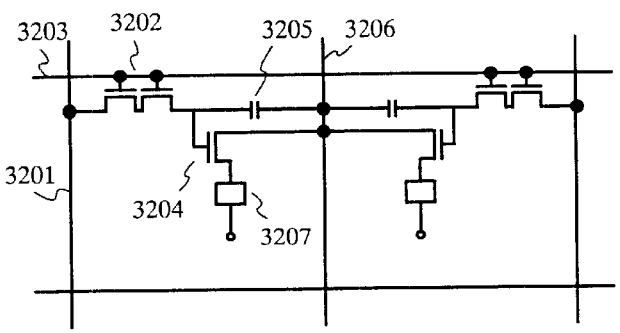
FIGS. 24A to 24C are views showing circuit structures for pixel portions in EL display devices of Embodiment 13 of the present invention.

In the embodiment of FIG. 24A, the current supply line 3206 is common to the two pixels. Specifically, this embodiment is characterized in that two pixels are lineal-symmetrically formed with the current supply line 3206 being the center between them. Since the number of current supply lines can be reduced therein, this embodiment is advantageous in that the pixel pattern can be much finer and thinner.

Figure 24B:
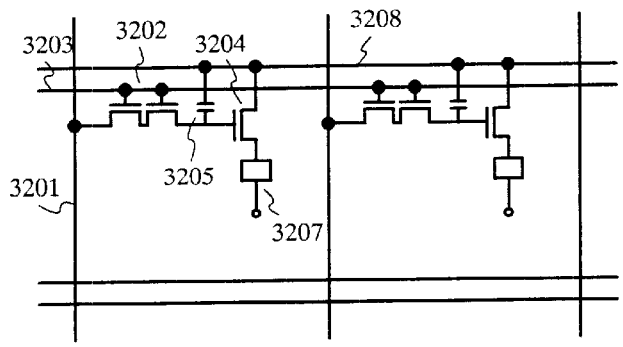

In the embodiment of FIG. 24B, the current supply line 3208 is formed in parallel to the gate wiring 3203. Specifically, in this, the current supply line 3208 is so constructed that it does not overlap with the gate wiring 3203, but is not limitative. Being different from the illustrated case, the two may overlap with each other via an insulating film therebetween so far as they are of different layers. Since the current supply line 3208 and the gate wiring 3203 may enjoy the common exclusive area therein, this embodiment is advantageous in that the pixel pattern can be much finer and thinner.

Figure 24C:
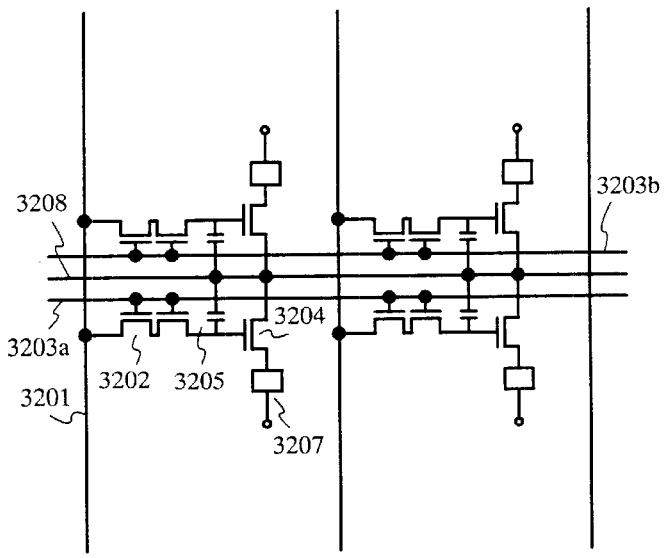

The structure of the embodiment of FIG. 24C is characterized in that the current supply line 3208 is formed in parallel to the gate wirings 3203, like in FIG. 24B, and that two pixels are lineal-symmetrically formed with the current supply line 3208 being the center between them. In this, it is also effective to provide the current supply line 3208 in such a manner that it overlaps with any one of the gate wirings 3203. Since the number of current supply lines can be reduced therein, this embodiment is advantageous in that the pixel pattern can be much finer and thinner.

Embodiment 14

The embodiment of Embodiment 11 illustrated in FIG. 22A and FIG. 22B is provided with the capacitor 3004 which acts to retain the voltage applied to the gate in the current-control TFT 3003. In the embodiment, however, the capacitor 3004 may be omitted.

In the embodiment of Embodiment 11, the current-control TFT 3003 is an NTFT with the LDD region being so formed that it overlaps with the gate electrode via the gate-insulating film therebetween. In the overlapped region, formed is a parasitic capacitance generally referred to as a gate capacitance. Embodiment 14 is characterized in that the parasitic capacitance is positively utilized in place of the capacitor 3004.

The parasitic capacitance varies, depending on the area in which the gate electrode overlaps with the LDD region, and is therefore determined according to the length of the LDD region in the overlapped area.

Also in the embodiments of Embodiment 13 illustrated in FIG. 24A, FIG. 24B and FIG. 24C, the capacitor 3205 can be omitted.

According to a goggle type display device system of the present invention, the system can see the condition of user's body based on user's vital information obtained by various sensors. If anomaly is recognized, first video signals given from an external device stop being displayed on LCD panels and outside scenery taken by the system is displayed instead. The user may be alarmed by this about anomaly of his or her body and, further, relaxed by looking at the outside scenery presented. Also, damage to user's eyesight may be prevented.

What is claimed is:

1. A goggle type display system comprising:

two display devices;

first video signals being inputted from an external video signal supplying device to display a first image on each of the two display devices;

two image capture elements for converting outside images into second video signals to display a second image on each of the two display devices;

a sensor for converting vital information of a user into a vital information signal; and a video signal control circuit for providing the two display devices with video signals, wherein the video signal control circuit provides the two display devices with the first video signals or the second video signals so that either the first image or the second image is determined to be displayed on each of the two display devices on the basis of an index being obtained by numerically processing the vital information signal.

2. A goggle type display system comprising:

two display devices;

first video signals being inputted from an external video signal supplying device to display a first image on each of the two display devices;

two first image capture elements for converting outside images into second video signals to display a second image on each of the two display devices;

two second image capture elements for converting images of user's eyes into third video signals;

a sensor for converting vital information of the user into a vital information signal; and a video signal control circuit for providing the two display devices with video signals, wherein the video signal control circuit provides the two display devices with the first video signals or the second video signals so that either the first image or the second image is determined to be displayed on each of the two display devices on the basis of an index being obtained by numerically processing the third video signals and the vital information signal.

3. A goggle type display system comprising:

two display devices;

first video signals being inputted from an external video signal supplying device to display a first image on each of the two display devices;

two image capture elements for converting outside images into second video signals to display a second image on each of the two display devices;

a sensor for converting vital information of a user into a vital information signal; and a video signal control circuit for providing the two display devices with video signals, wherein the video signal control circuit calculates a degree of fatigue of the user on the basis of a chaos attractor index being obtained by numerically processing the vital information signal, wherein the video signal control circuit provides the two display devices with the first video signals to display the first image on each of the two display devices when the degree of fatigue is equal to or less than a predetermined level, and wherein the video signal control circuit provides the two display devices with the second video signals to display the second image on each of the two display devices when the degree of fatigue exceeds the predetermined level.

4. A goggle type display system comprising:

two display devices;

first video signals being inputted from an external video signal supplying device to display a first image on each of the two display devices;

two first image capture elements for converting outside images into second video signals to display a second image on each of the two display devices;

two second image capture elements for converting images of user's eyes into third video signals;

a sensor for converting vital information of a user into a vital information signal; and a video signal control circuit for providing said two display devices with video signals, wherein the video signal control circuit calculates a degree of fatigue of the user on the basis of a chaos attractor index being obtained by numerically processing the third video signals and the vital information signal, wherein the video signal control circuit provides the two display devices with the first video signals to display the first image on each of the two display devices when the degree of fatigue is equal to or less than a predetermined level, and wherein the video signal control circuit provides the two display devices with the second video signals to display the second image on each of the two display devices when the degree of fatigue exceeds the predetermined level.

5. A system according to claim 1, wherein each of the image capture elements is a CCD image capture element or an image sensor.

6. A system according to claim 2, wherein each of the second image capture elements is a CCD image capture element or an image sensor.

7. A system according claim 1, wherein the vital information of the user is at least one selected from the group consisting of pulse wave, blood pressure, body temperature and dilated degree of the pupils of the eyes.

8. A system according to claim 1, wherein the sensor is at least one selected from the group consisting of a pulse wave sensor, a blood pressure sensor and a body temperature sensor.

9. A system according to claim 8, wherein the sensor is arranged in a headphone.

10. A system according to claim 5, wherein the image sensor is formed integrally with each of the display devices.

11. A system according to claim 1, wherein each of the display devices is a reflection type liquid crystal display device.

12. A system according to claim 1, wherein each of the display devices has a back light using red LEDs, green LEDs and blue LEDs.

13. A system according to claim 12, wherein each of the display devices is operated by a field sequential system.

14. A system according to claim 2, wherein each of the first image capture elements is a CCD image capture element or an image sensor.

15. A system according claim 2, wherein the vital information of the user is at least one selected from the group consisting of pulse wave, blood pressure, body temperature and dilated degree of the pupils of the eyes.

16. A system according to claim 2, wherein the sensor is at least one selected from the group consisting of a pulse wave sensor, a blood pressure sensor and a body temperature sensor.

17. A system according to claim 16, wherein the sensor is arranged in a headphone.

18. A system according to claim 14, wherein the image sensor is formed integrally with each of the display devices.

19. A system according to claim 2, wherein each of the display devices is a reflection type liquid crystal display device.

20. A system according to claim 2, wherein each of the display devices has a back light using red LEDs, green LEDs and blue LEDs.

21. A system according to claim 20, wherein each of the display devices is operated by a field sequential system.

22. A system according to claim 3, wherein each of the image capture elements is a CCD image capture element or an image sensor.

23. A system according claim 3, wherein the vital information of the user is at least one selected from the group consisting of pulse wave, blood pressure, body temperature and dilated degree of the pupils of the eyes.

24. A system according to claim 3, wherein the sensor is at least one selected from the group consisting of a pulse wave sensor, a blood pressure sensor and a body temperature sensor.

25. A system according to claim 24, wherein the sensor is arranged in a headphone.

26. A system according to claim 22, wherein the image sensor is formed integrally with each of the display devices.

27. A system according to claim 3, wherein each of the display devices is a reflection type liquid crystal display device.

28. A system according to claim 3, wherein each of the display devices has a back light using red LEDs, green LEDs and blue LEDs.

29. A system according to claim 28, wherein each of the display devices is operated by a field sequential system.

30. A system according to claim 4, wherein each of the first image capture elements is a CCD image capture element or an image sensor.

31. A system according to claim 4, wherein each of the second image capture elements is a CCD image capture element or an image sensor.

32. A system according claim 4, wherein the vital information of the user is at least one selected from the group consisting of pulse wave, blood pressure, body temperature and dilated degree of the pupils of the eyes.

33. A system according to claim 4, wherein the sensor is at least one selected from the group consisting of a pulse wave sensor, a blood pressure sensor and a body temperature sensor.

34. A system according to claim 33, wherein the sensor is arranged in a headphone.

35. A system according to claim 30, wherein the image sensor is formed integrally with each of the display devices.

36. A system according to claim 31, wherein the image sensor is formed integrally with each of the display devices.

37. A system according to claim 4, wherein each of the display devices is a reflection type liquid crystal display device.

38. A system according to claim 4, wherein each of the display devices has a back light using red LEDs, green LEDs and blue LEDs.

39. A system according to claim 38, wherein each of the display devices is operated by a field sequential system.

40. A system according to claim 6, wherein the image sensor is formed integrally with each of the display devices.

41. A system according to claim 1, wherein each of the display devices is a liquid crystal display device.

42. A system according to claim 1, wherein each of the display devices is an EL display device.

43. A system according to claim 2, wherein each of the display devices is a liquid crystal display device.

44. A system according to claim 2, wherein each of the display devices is an EL display device.

45. A system according to claim 3, wherein each of the display devices is a liquid crystal display device.

46. A system according to claim 3, wherein each of the display devices is an EL display device.

47. A system according to claim 4, wherein each of the display devices is a liquid crystal display device.

48. A system according to claim 4, wherein each of the display devices is an EL display device.

* * * * *